United States Patent
Rottler et al.

(10) Patent No.: US 8,512,211 B2
(45) Date of Patent: Aug. 20, 2013

(54) METHOD FOR QUICKSTART WORKOUT GENERATION AND CALIBRATION

(75) Inventors: Benjamin Andrew Rottler, Burlingame, CA (US); Allen P. Haughay, Jr., San Jose, CA (US); Ryan Perry, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 1323 days.

(21) Appl. No.: 12/205,302

(22) Filed: Sep. 5, 2008

(65) Prior Publication Data
US 2010/0062905 A1  Mar. 11, 2010

(51) Int. Cl.
*A63B 71/00* (2006.01)

(52) U.S. Cl.
USPC ........................................ 482/9; 482/1; 482/8

(58) Field of Classification Search
USPC .......................................................... 482/1–9
See application file for complete search history.

(56) References Cited

U.S. PATENT DOCUMENTS

| | | | |
|---|---|---|---|
| 4,375,674 A * | 3/1983 | Thornton | 702/41 |
| 4,649,552 A | 3/1987 | Yukawa | |
| 4,830,021 A * | 5/1989 | Thornton | 600/520 |
| 4,884,445 A * | 12/1989 | Sadoff et al. | 73/379.02 |
| 5,348,519 A * | 9/1994 | Prince et al. | 482/6 |
| 5,391,080 A * | 2/1995 | Bernacki et al. | 434/254 |
| 5,471,405 A | 11/1995 | Marsh | |
| 5,524,637 A * | 6/1996 | Erickson | 600/592 |
| 5,583,776 A * | 12/1996 | Levi et al. | 701/400 |
| 5,615,132 A * | 3/1997 | Horton et al. | 703/7 |
| 5,963,891 A * | 10/1999 | Walker et al. | 702/150 |
| 5,976,083 A * | 11/1999 | Richardson et al. | 600/300 |
| 6,013,007 A | 1/2000 | Root et al. | |
| 6,032,108 A | 2/2000 | Seiple et al. | |
| 6,073,086 A * | 6/2000 | Marinelli | 702/141 |
| 6,135,951 A | 10/2000 | Richardson et al. | |
| 6,145,389 A * | 11/2000 | Ebeling et al. | 73/865.4 |
| 6,224,512 B1 * | 5/2001 | Arnesson | 482/5 |
| 6,238,338 B1 * | 5/2001 | DeLuca et al. | 600/300 |
| 6,323,846 B1 | 11/2001 | Westerman et al. | |
| 6,357,147 B1 | 3/2002 | Darley et al. | |
| 6,456,261 B1 * | 9/2002 | Zhang | 345/8 |
| 6,463,385 B1 | 10/2002 | Fry | |

(Continued)

FOREIGN PATENT DOCUMENTS

WO  02/093272  11/2002

OTHER PUBLICATIONS

U.S. Appl. No. 12/030,774, filed Feb. 13, 2008, Kruger et al.

*Primary Examiner* — Loan Thanh
*Assistant Examiner* — Sundhara Ganesan
(74) *Attorney, Agent, or Firm* — Fletcher Yoder PC

(57) ABSTRACT

Systems and methods for generating a quick start workout template and calibrating an electronic device using the workout template are provided. The electronic device may create and store a workout template to be used in conjunction with a workout. The workout template may be selected in a quick start fashion to restart the same workout. The workout template may be defined at least in part by a selection of any suitable workout goal and/or any suitable associated media. If the media associated with the workout goal is changed or is removed, a new workout template may be created. The electronic device may be calibrated or recalibrated using the workout template. If the electronic device is calibrated or re-calibrated with respect to a particular sensor, the electronic device may use the calibration in conjunction with any suitable workout template and the sensor to more accurately monitor the user's workout.

11 Claims, 13 Drawing Sheets

(56) References Cited

U.S. PATENT DOCUMENTS

| | | |
|---|---|---|
| 6,539,336 B1 | 3/2003 | Vock et al. |
| 6,560,903 B1 | 5/2003 | Darley |
| 6,582,342 B2 | 6/2003 | Kaufman |
| 6,611,789 B1 * | 8/2003 | Darley .......... 702/160 |
| 6,619,835 B2 | 9/2003 | Kita |
| 6,716,139 B1 | 4/2004 | Hosseinzadeh-Dolkhani et al. |
| 6,735,630 B1 * | 5/2004 | Gelvin et al. .......... 709/224 |
| 6,790,178 B1 | 9/2004 | Mault et al. |
| 6,793,607 B2 | 9/2004 | Neil |
| 6,885,971 B2 * | 4/2005 | Vock et al. .......... 702/182 |
| 6,898,550 B1 | 5/2005 | Blackadar et al. |
| 7,030,735 B2 | 4/2006 | Chen |
| 7,062,225 B2 | 6/2006 | White |
| 7,171,331 B2 | 1/2007 | Vock et al. |
| 7,174,227 B2 | 2/2007 | Kobayashi et al. |
| 7,200,517 B2 | 4/2007 | Darley et al. |
| 7,251,454 B2 | 7/2007 | White |
| 7,254,516 B2 * | 8/2007 | Case et al. .......... 702/182 |
| 7,278,966 B2 | 10/2007 | Hjelt et al. |
| 7,292,867 B2 | 11/2007 | Werner et al. |
| 7,353,139 B1 | 4/2008 | Burrell et al. |
| 7,454,002 B1 | 11/2008 | Gardner et al. |
| 7,519,327 B2 | 4/2009 | White |
| 7,618,345 B2 | 11/2009 | Corbalis et al. |
| 7,670,263 B2 | 3/2010 | Ellis et al. |
| 8,166,028 B1 * | 4/2012 | Reynar et al. .......... 707/732 |
| 2002/0077784 A1 | 6/2002 | Vock et al. |
| 2003/0097878 A1 | 5/2003 | Farringdon et al. |
| 2003/0208113 A1 | 11/2003 | Mault et al. |
| 2004/0073325 A1 * | 4/2004 | Reeves .......... 700/91 |
| 2004/0128007 A1 * | 7/2004 | Shiratori .......... 700/91 |
| 2005/0172311 A1 | 8/2005 | Hjelt et al. |
| 2007/0270721 A1 | 11/2007 | Ananny et al. |
| 2007/0271065 A1 | 11/2007 | Gupta et al. |
| 2007/0271387 A1 | 11/2007 | Lydon et al. |
| 2009/0209358 A1 * | 8/2009 | Niegowski .......... 473/223 |

* cited by examiner

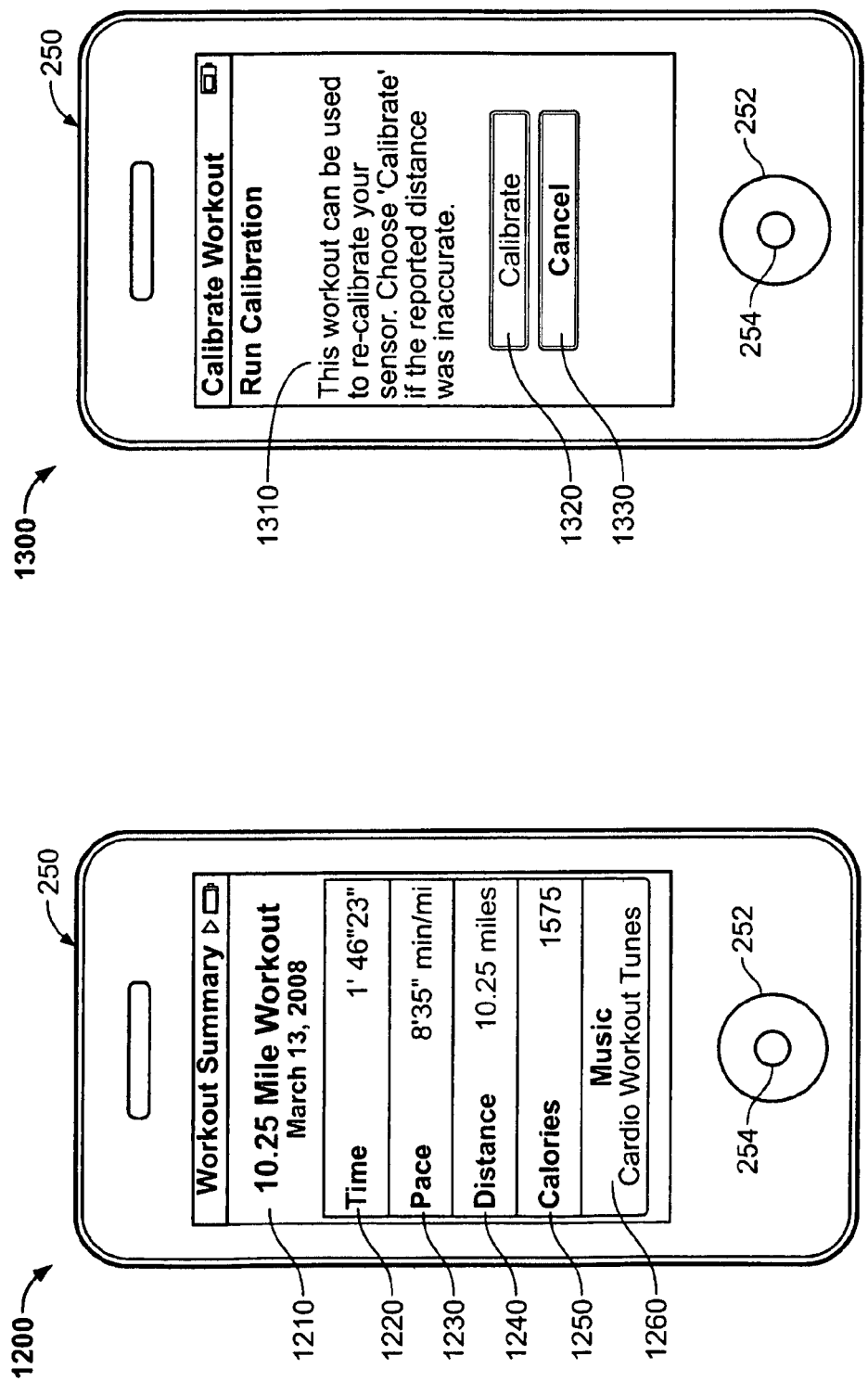

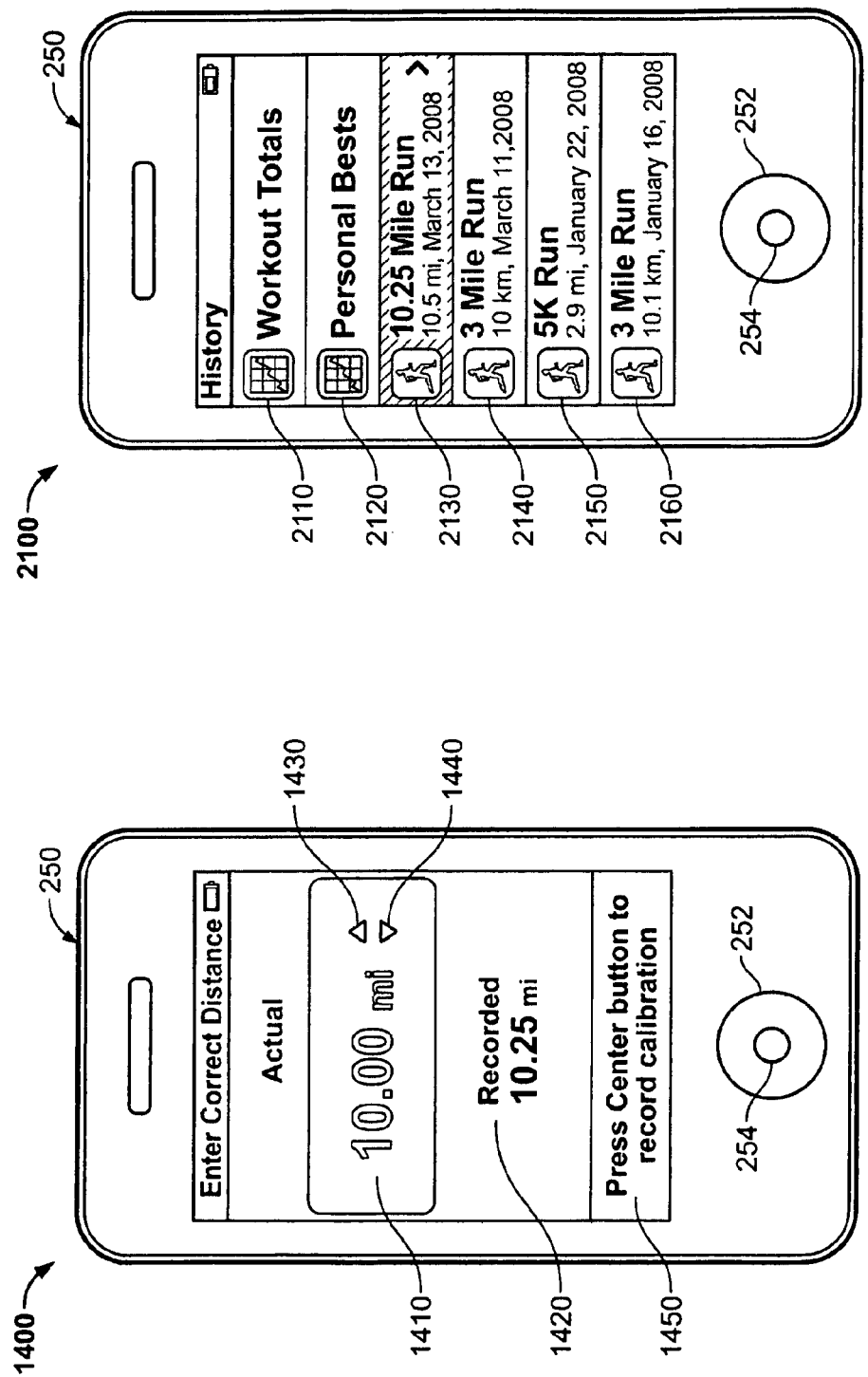

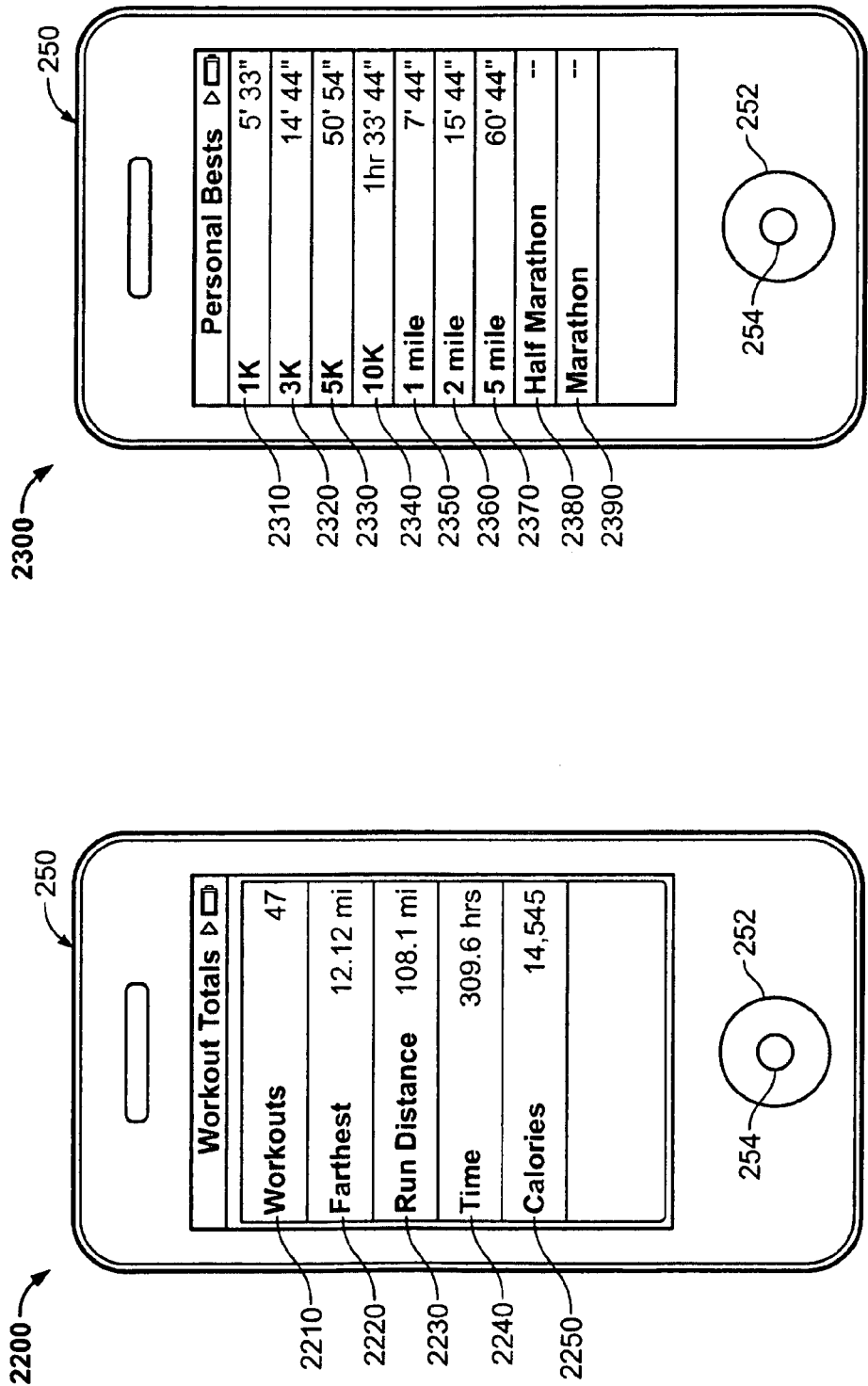

METHOD FOR QUICKSTART WORKOUT GENERATION AND CALIBRATION

FIELD OF THE INVENTION

This relates to systems and methods for generating a quick start workout template and calibrating an electronic device using the workout template.

BACKGROUND OF THE DISCLOSURE

Currently, an electronic device may allow a user to choose a type of athletic workout and the electronic device may also play back one or more media items to accompany the workout. The electronic device may provide information about the workout in real time to a user, in conjunction with a sensor that may transmit the information to the electronic device. However, a new workout and new media must be selected each time that the user wishes to use the electronic device during the workout, even if the newly-selected workout or media match a previous workout selection or prior media selections made by the user using the electronic device.

Therefore, it would be beneficial to provide systems and methods for storing a workout and related media selections as a template for future "quick start" selection by the user. The systems and methods may include storing a change of media within a new workout template. In addition, it would also be beneficial to provide systems and methods for calibrating or re-calibrating an electronic device using a completed workout.

SUMMARY OF THE DISCLOSURE

Systems and methods for generating a quick start workout template and calibrating an electronic device using the workout template are provided. In one embodiment, an electronic device for performing a workout using a workout template is provided. The electronic device may include a storage component and control circuitry coupled to the storage component. The control circuitry may be operative to define the workout template that may include at least one workout goal and at least one media item associated with the at least one workout goal, store the workout template in the storage component, and start the workout in response to a selection of the stored workout template.

In one embodiment, a method for performing a workout using a workout template is provided. The method may include defining the workout template that may include at least one workout goal and at least one media item associated with the at least one workout goal, storing the workout template, selecting the workout template, and starting the workout in response to selecting the stored workout template.

In one embodiment, a method for calibrating an electronic device is provided. The method may include storing a workout and at least one workout statistic on the electronic device, presenting a workout menu in response to the storing the workout and the at least one workout statistic, selecting a calibration option from the workout menu, presenting a calibration program with the at least one workout statistic in response to the selecting the calibration option, adjusting the at least one workout statistic using the calibration program, and storing the adjusted at least one workout statistic with the workout in the electronic device.

In one embodiment, an electronic device for calibrating a workout is provided. The electronic device may include a storage component and control circuitry coupled to the storage component. The control circuitry may be operative to generate at least one workout statistic from the workout, store the workout and the at least one workout statistic in the storage component, present at least one workout option, present a calibration program with the at least one workout statistic in response to a selection of the at least one workout option, adjust a reported value of the at least one workout statistic to correspond to an actual value of the at least one workout statistic, and store the adjusted at least one workout statistic with the workout in the storage component.

BRIEF DESCRIPTION OF THE DRAWINGS

The above and other aspects and advantages of the invention will become more apparent upon consideration of the following detailed description, taken in conjunction with the accompanying drawings, in which like reference characters refer to like parts throughout, and in which:

FIG. 12 is a front view of an electronic device with an illustrative display screen for viewing a workout summary in accordance with some embodiments of the invention;

FIG. 13A is a front view of an electronic device with an illustrative display screen for calibrating an electronic device in accordance with some embodiments of the invention;

FIG. 14 is a front view of an electronic device with an illustrative display screen for defining a calibration in accordance with some embodiments of the invention;

FIG. 15 is a front view of an electronic device with an illustrative display screen for selecting a workout history in accordance with some embodiments of the invention;

FIG. 16 is a front view of an electronic device with an illustrative display screen for reviewing a summary of workouts in accordance with some embodiments of the invention;

FIG. 17 is a front view of an electronic device with an illustrative display screen for reviewing a summary of workout statistics in accordance with some embodiments of the invention;

DETAILED DESCRIPTION OF THE DISCLOSURE

Figure 1A:
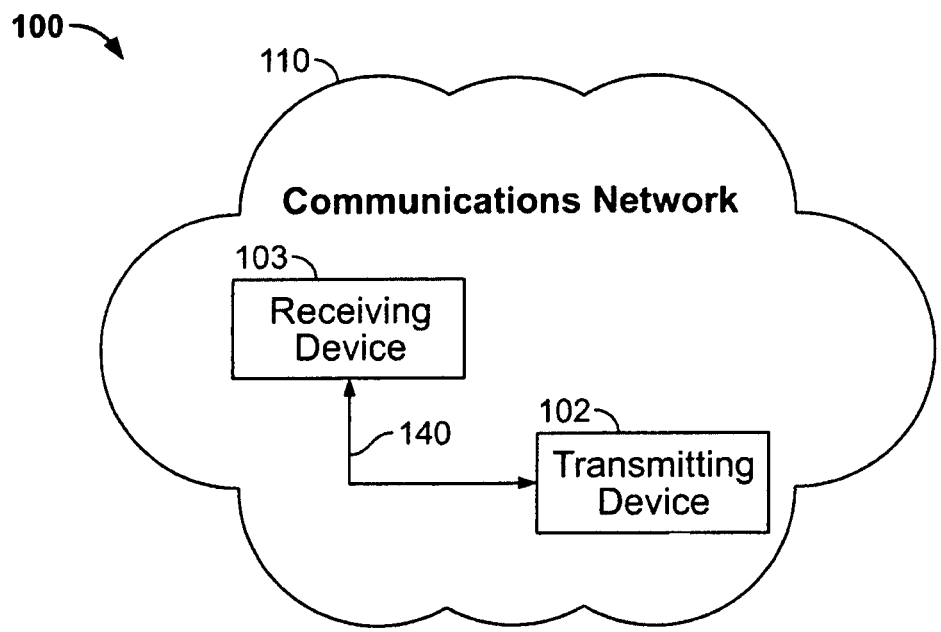
FIG. 1A is a schematic view of a communications system in accordance with some embodiments of the invention.

In some embodiments of the invention, an electronic device capable of creating and storing a workout template, and being calibrated using the workout template, may be provided. Once a workout template is created and stored, a user may select the template in a quick start fashion to restart the same workout. It is to be understood that "quick start" selection of a workout template by a user of the electronic device may include any suitable number of inputs from a user to make the selection, including for example, only one input (e.g., one click or one touch input gesture by the user). The invention may be employed with any user input-driven electronic device that also may include any suitable type of display screen. The electronic device also may include any suitable mechanism or circuitry (e.g., a receiver) for receiving and processing signals from a transmitting device, such as a sensor. The signals may contain any suitable information about a user's workout. The receiver may be coupled to the electronic device in any suitable manner, or the receiver may be included within the electronic device (e.g., as part of the circuitry). The sensor may be linked to the electronic device in any suitable manner, and the sensor also may be coupled to the user in any suitable manner, such as being affixed to the user's shoe or to an exercise machine used by the user. The electronic device may be used to create, review, and organize new workout templates, review workout template settings stored in the electronic device, and perform calibration activities.

In some embodiments of the invention, creation and storage of a workout template on the electronic device may be provided. The workout template may be defined at least in part by a selection of any suitable number of workout goals by the user. For example, the workout goal may include a time elapsed, distance traveled, calories burned, desired pace, a particular activity on an exercise machine, or any other suitable goal. One or more workout goals may be defined using a default value stored within the electronic device or may be defined using any suitable custom value selected by the user. The workout template also may include any suitable media playlist or playlists to accompany the selected workout goal or goals. Each media playlist may include any suitable number of media items of any suitable media type, including music, videos, photographs, podcasts, other audio or video files, or any other suitable media types or combinations of media types therein. Playlists or individual media items may be presented to the user in any suitable order, such as in alphabetical order, in order of predominant media type, in forward or reverse chronological order of date compiled or date stored in the electronic device, in order of the user's preference (e.g., the most frequently selected playlists or media items may be presented first), in order of mood types that may be associated with a particular playlist or media item, or in any other suitable order.

In some embodiments, a user may designate any suitable number of media items (e.g., a song, a video, a photograph) as "PowerMedia" items, which the user may select for playback at any time during any workout regardless of what workout template is currently being used with the workout or regardless of when the PowerMedia item is selected during the workout. If the media associated with any of the workout goals is changed or is removed from the template, a new workout template may be created using the same workout goal or goals associated with the changed media or associated with no media. In some embodiments, one or more of the workout templates stored in the electronic device may not associate media with the workout goal or goals. Once a user selects any suitable media to associate with the workout goal or goals, or chooses not to associate media, the user may review the newly defined workout template using any suitable approach.

The new workout template, once approved, may be stored in the electronic device for future quick start selection and for future review. As a workout progresses on the electronic device using the workout template, the template may be populated with statistics related to that workout. The sensor may transmit signals containing information related to the workout that the electronic device may store as workout statistics (e.g., distance traveled, time elapsed, number of calories burned, or pace achieved). In some embodiments, the user may stop the playback of media during a workout, or stop or pause the workout, using any suitable method.

Workout statistics generated from the workout may be stored in the electronic device and the user may review these statistics in the future, or may compare these statistics to statistics related to another prior workout stored within the electronic device. In some embodiments, the statistics may be transmitted (e.g., uploaded) to a remote source for sharing with other users. The workout template may be selected again in the future as a quick start workout option and information from the second use of the workout template may also be stored in the electronic device. In some embodiments, the workout template may be generated after the user completes a workout. When the user's workout is complete or otherwise ended, the electronic device may permit the user to create a workout template using a completed workout goal and any accompanying media to define the workout template.

In some embodiments of the invention, calibration or recalibration of the electronic device using the workout template may be provided. For example, the user may complete a workout using the workout template and may be shown the statistics related to the workout. After reviewing the workout statistics, the user may realize that one or more of the reported statistics is incorrect. The reported statistic may be corrected in any suitable manner, which also results in a calibration of the electronic device, including, for example, by adjusting the reported value of the workout statistic until it reflects the actual value of the statistic for that workout. If the electronic device is calibrated or re-calibrated with respect to workout information transmitted from a particular sensor, the electronic device may use the calibration in conjunction with any suitable workout template and with the sensor to more accurately monitor the user's future workouts. In some embodiments, the electronic device may alter prior stored calibrations in addition to performing a new calibration.

In some embodiments of the invention, the electronic device may perform a calibration or recalibration with respect to any type of movement that may be calibrated on the electronic device using a calibration template (e.g., a selected calibration exercise and, in some embodiments, at least one associated media item). Signal information received from the sensor linked to the electronic device with respect to one type of exercise movement (e.g., walking) may not resemble signal information received with respect to a different type of exercise movement (e.g., running). Thus, the electronic device may be calibrated with respect to any suitable type of exercise movement that the linked sensor may detect. In some embodiments, any type of movement that has already been calibrated on the electronic device may be recalibrated with respect to a particular sensor that may be linked to the electronic device. Information generated from the calibration using the calibration template may be stored in the electronic device for future application with suitable workout templates and the linked sensor. The user may review the results of the calibration, including any suitable information relevant to the calibration template, such as time elapsed, pace, distance traveled, calories burned, and any other suitable information.

In some embodiments of the invention, the user may review prior workouts and related statistics in any suitable manner. For example, the user may review statistics related to an individual prior workout such as the time taken to complete the workout, an activity achieved on a particular exercise machine, the pace, the distance traveled, and/or the calories burned during the workout. In some embodiments, media that may be associated with the workout may also be reviewed. The user may review accumulated workout statistics related to all of the workouts that may be stored in the electronic device and the user also may review personal best statistics that may be compiled from all of the stored workouts. In some embodiments, the user may quick start a prior stored workout after reviewing statistics related to the workout.

Systems and methods for generating a quick start workout template and calibrating an electronic device using the workout template are provided and described with reference to FIGS. 1-20.

FIG. 1A is a schematic view of a communications system in accordance with some embodiments of the invention. Communications system 100 may include a transmitting device 102 that initiates a signal and communications network 110, which transmitting device 102 may use to send transmissions to other communications devices within communications network 110. For example, communications system 100 may include a receiving device 103 capable of receiving a transmission from transmitting device 102. Although communications system 100 may include several transmitting devices 102 and receiving devices 103, only one of each is shown in FIG. 1A to simplify the drawing.

Any suitable circuitry, device, system or combination of these (e.g., a wireless communications infrastructure including communications towers and telecommunications servers) operative to create a communications network may be used to create communications network 110. Communications network 110 may be capable of providing communications using any suitable communications protocol. In some embodiments, communications network 110 may support, for example, traditional telephone lines, cable television, Wi-Fi™ (e.g., a 802.11 protocol), Bluetooth™, Nordic high frequency systems (e.g., 900 MHz, 2.4 GHz, and 5.6 GHz communication systems), infrared, other relatively localized wireless communication protocol, or any combination thereof. In some embodiments, communications network 110 may support protocols used by wireless and cellular phones and personal e-mail devices (e.g., a Blackberry™ available from Research In Motion Limited of Waterloo, Ontario). Such protocols can include, for example, GSM, GSM plus EDGE, CDMA, quadband, and other cellular protocols. Transmitting device 102 and receiving device 103, when located within communications network 110, may communicate over a bidirectional communication path such as path 140. In some embodiments, transmitting device 102 and receiving device 103 may communicate wirelessly, as described more fully in U.S. Patent Publication No. 2007/0271387, published Nov. 22, 2007, entitled "Communication Protocol For Use With Portable Electronic Devices," and as described more fully in U.S. patent application Ser. No. 12/030,774, filed Feb. 13, 2008, entitled "Method of Using Bluetooth Module To Process Non-Bluetooth Signals," each of which is incorporated by reference herein in its entirety.

Transmitting device 102 may include any suitable device for transmitting any suitable type of signal. For example, transmitting device 102 may include a sensor or a machine (e.g., an exercise machine) capable of transmitting a signal at a particular frequency. In some embodiments, the sensor may be placed in any suitable location relative to receiving device 103 (e.g., within the shoe of a user of receiving device 103) and may transmit a signal to receiving device 103 even as the sensor is moving. Receiving device 103 may include any suitable device for receiving any suitable type of signal from transmitting device 102. For example, receiving device 103 may include a media player such as an iPod™, an iPod™ nano, an iPod Touch™, or iPhone™ available from Apple Inc., of Cupertino, Calif., a cellular telephone, a personal e-mail or messaging device (e.g., a Blackberry™ available from Research In Motion Limited of Waterloo, Ontario), pocket-sized personal computers (e.g., an iPAQ™ Pocket PC available by Hewlett Packard Inc. of Palo Alto, Calif.), personal digital assistants (PDAs), a desktop computer, a laptop computer, or any other device capable of communicating wirelessly (with or without the aid of a wireless enabling accessory system) or via wired pathways (e.g., using traditional telephone wires). The signal may include any suitable form of signal, including, for example, a radio signal or a digital signal. The signal may include any suitable information, including, for example, exercise information related to the movement of a user of receiving device 103.

Figure 1B:
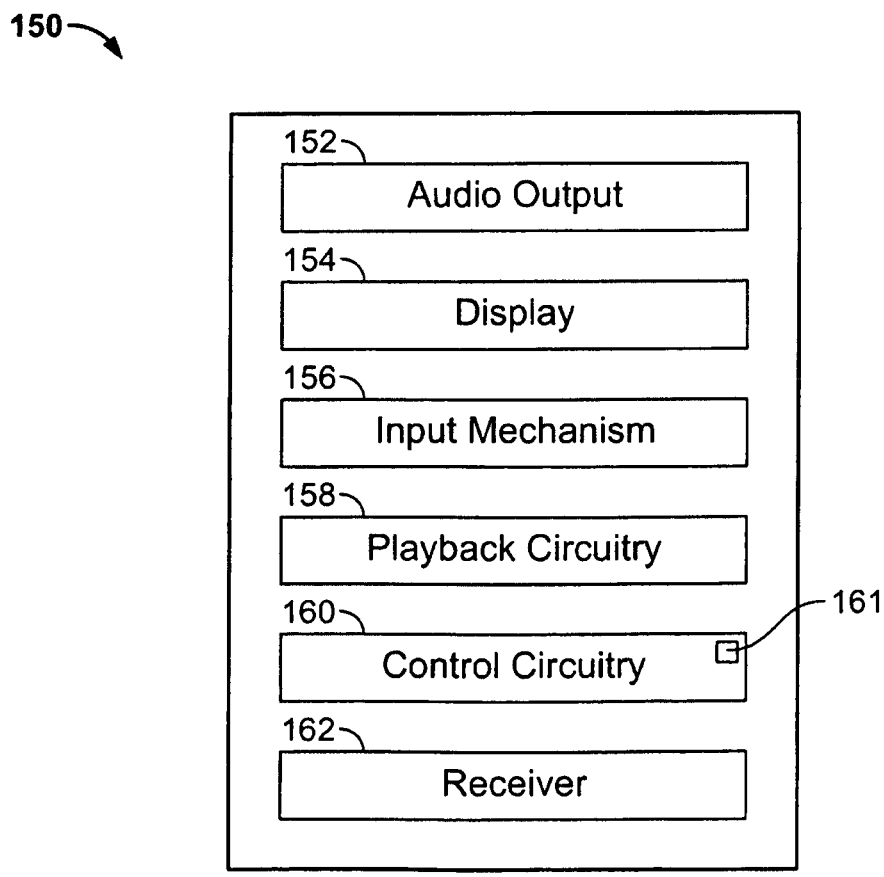
FIG. 1B is a schematic view of an electronic device in accordance with some embodiments of the invention.

FIG. 1B is a schematic view of an electronic device in accordance with some embodiments of the invention. The electronic device may include any suitable device for receiving inputs, and for transmitting and receiving signals from transmitting device 102 (FIG. 1A). For example, electronic device 150 may include a desktop computer, a laptop computer, a device capable of communicating wirelessly (with or without the aid of a wireless enabling accessory system) or via wired pathways (e.g., using traditional electrical wires), a pocket-sized personal computer (e.g., an iPAQ™ Pocket PC available by Hewlett Packard Inc. of Palo Alto, Calif.), a personal digital assistant ("PDA"), a personal e-mail or messaging device with audio and/or video capabilities (e.g., a Blackberry™ available from Research In Motion Limited of Waterloo, Ontario), or an iPod™, an iPod™ nano, an iPod Touch™ or an iPhone™ available by Apple Inc. of Cupertino, Calif. The input may include any suitable form of instruction, including for example, voice instruction (e.g., a spoken command), data instruction, manual instruction (e.g., a keystroke, a click or a touch input gesture by the user), an instruction from a program installed in electronic device 150, an instruction based upon a sensed condition (e.g., an input related to a signal transmitted by transmitting device 102), or combinations thereof.

Electronic device 150 may include audio output 152, display 154, input mechanism 156, playback circuitry 158, control circuitry 160, storage component 161, receiver 162, and any other suitable components. All of the applications employed by audio output 152, display 154, input mechanism 156, playback circuitry 158, storage component 161, and receiver 162 may be interconnected and managed by control circuitry 160.

Audio output 152 may include any suitable audio component for providing audio to the user of electronic device 100. For example, audio output 152 may include one or more speakers (e.g., mono or stereo speakers) built into electronic device 150. In some embodiments, audio output 152 may include an audio component that is remotely coupled to electronic device 150. For example, audio output 152 may include a headset, headphones or earbuds that may be coupled to electronic device 150 with a wire (e.g., coupled to electronic device 150 with a jack) or wirelessly (e.g., Bluetooth™ headphones or a Bluetooth™ headset).

Display 154 may include any suitable screen or projection system for providing a display visible to the user. For example, display 154 may include a screen (e.g., an LCD screen) that is incorporated in electronic device 150. As another example, display 154 may include a movable display or a projecting system for providing a display of content on a surface remote from electronic device 150 (e.g., a video projector). Display 154 may be operative to display content (e.g., information regarding a user's current workout) under the direction of control circuitry 160.

Input mechanism 156 may be any suitable mechanism for providing user inputs or instructions to electronic device 150. Input mechanism 156 may take a variety of forms, such as a touch screen, a button, keypad, dial, or a click wheel. The user interface may include a multi-touch screen such as that described in U.S. Pat. No. 6,323,846, which is incorporated by reference herein in its entirety. In some embodiments, input mechanism 156 may include any suitable mechanism (e.g., a microphone) that may be coupled to electronic device 150 or included within electronic device 150 and that may be operative to receive a voice instruction (e.g., a spoken command) as an input and transmit the input to control circuitry 160.

Playback circuitry 158 may be any suitable circuitry operative to read, classify, store, play and transmit different types of media to an active output such as audio output 152 (e.g., audio) or display 154 (e.g., video) at the direction of control circuitry 160. Playback circuitry 158 may be operative to interface with control circuitry 160 to play any suitable media item, or any suitable number of media items either continuously or simultaneously, as selected by a user of electronic device 150. In some embodiments, playback circuitry 158 may be incorporated in control circuitry 160.

Control circuitry 160 may be operative to control the operations and performance of electronic device 150. Control circuitry 160 may include, for example, a processor, a bus (e.g., for sending instructions to the other components of electronic device 150), memory, storage component 161, or any other suitable component for controlling the operations of electronic device 150. In some embodiments, a processor may drive the display and process inputs received from the user interface (e.g., the click-wheel or touch screen). The memory and storage component 161 may include, for example, cache, Flash, ROM, and/or RAM. In some embodiments, memory may be specifically dedicated to storing firmware (e.g., for device applications such as an operating system, user interface functions, and processor functions). In some embodiments, memory may be operative to store a media item in storage component 161 that electronic device 150 may download from a host system. Alternatively, control circuitry 160 may stream the media item from a source to make the media item available for playback without storing the media item in storage component 161.

Control circuitry 160 may be operative to perform the operations of one or more applications implemented on electronic device 150. Any suitable number or type of applications may be implemented. Although the following discussion will enumerate different applications, it will be understood that some or all of the applications may be combined into one or more applications. In some embodiments, electronic device 150 may include one or several applications operative to store any suitable number of workout templates, monitor a user's workout, perform a calibration, and download and/or play a variety of stored or streaming media items (e.g., songs, videos, movies, photographs), individually or simultaneously.

Receiver 162 may include any suitable mechanism operative to detect a signal from a sensor (e.g., transmitting device 102) and to send the signal to control circuitry 160 for further processing. In some embodiments, receiver 162 may be detachable from electronic device 150 and may be coupled to electronic device 150 in any suitable manner (e.g., an accessory coupled to a bottom face of electronic device 150). Alternatively, in some embodiments, receiver 162 may be included within control circuitry 160.

Control circuitry 160 may include additional circuitry (e.g., logic circuitry) that may analyze the signal information received from transmitting device 102. For example, the signal may contain information related to a user's current workout, such as the pace of the workout, time elapsed, distance traveled, calories burned, a user's activity on a particular exercise machine or any other suitable information. Control circuitry 160 may have stored a workout template that may be created by the user and may be populated with workout statistics generated from the signal information as the workout progresses. Control circuitry 160 may store the workout statistics with the particular workout for future review and analysis by the user. Likewise, control circuitry 160 also may store information related to a calibration of electronic device 150 based upon the workout that may be populated with signal information received from transmitting device 102. In addition, control circuitry 160 may include circuitry (e.g., communications circuitry) to allow a user to upload the workout statistics generated from the signal information to a remote host system, such as a computer network.

An electronic device may store a workout template, including associated media, for future quick start selection by a user. The electronic device may also be calibrated or recalibrated using the workout template in a quick start fashion. FIGS. 2-17 are front views of an electronic device 250 with various illustrative display screens 200-2300 that may be displayed as the electronic device creates, stores, and uses one or more quick start workout templates. Display screens 200-2300 may include any suitable orientation, such as a portrait-type orientation as shown, or a landscape-type orientation (not shown), which may depend on the shape and orientation of electronic device 250 relative to each display screen. Similarly, one or more options may be displayed on electronic device 250 during any workout in a portrait or landscape fashion, and the orientation of the options may depend on the workout template being applied to the current workout. The electronic device 250 of each of FIGS. 2-17 may be the same as or different from, and may include some or all of the features of, electronic device 150 (FIG. 1B). For example, click or scroll wheel 252 and button 254 in each of FIGS. 2-17 may be the same as, and may include some or all of the features of, input mechanism 156. Once a workout template is created, a user may select the template in the future to restart the same workout using the same or different media selections. The user may provide inputs to the electronic device using any suitable input mechanism, including for example an interface that includes a touch screen, a "home" button, a click wheel, combinations thereof, or any other suitable input mechanism.

Figure 2:
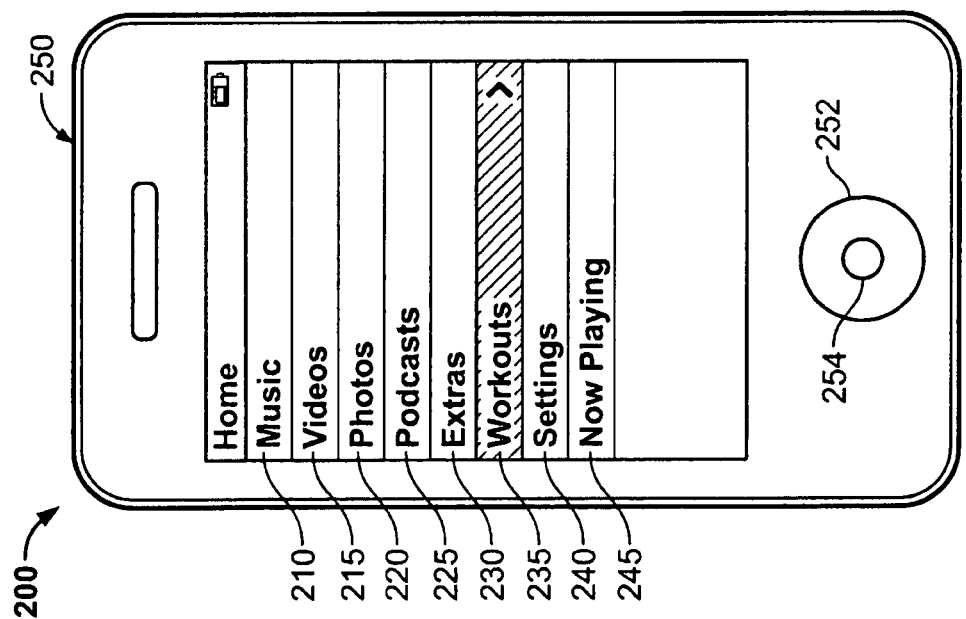
FIG. 2 is a front view of an electronic device with an illustrative display screen for selecting a workout application in accordance with some embodiments of the invention.

FIG. 2 is a front view of electronic device 250 with an illustrative display screen 200 for selecting a workout application in accordance with some embodiments of the invention. Display screen 200 may be displayed when electronic device 250 is turned on (e.g., display screen 200 may represent the "home" screen of electronic device 250). Display screen 200 may include several selectable options for operating different applications of electronic device 250. Options may include, for example, Music option 210, Videos option 215, Photos option 220, Podcasts option 225, Extras option 230, Workouts option 235, Settings option 240, Now Playing option 245, or any other suitable option. One or more of the options may appear on display screen 200 regardless of the application being operated by electronic device 250.

A user of electronic device 250 may select Music option 210 to listen to, download, organize and store music media items on electronic device 250. Videos option 215 may be selected to display and organize video media stored within electronic device 250 or capable of being streamed to electronic device 250 for viewing. Photos option 220 may allow the user to display and organize photographs captured by, stored in, or streamed to electronic device 250. Podcasts option 225 may allow the user to display, listen to, organize, and review podcasts stored in or streamed to electronic device 250. Workouts option 235 may be selected to create, select, review, organize, and upload workout templates that may also be used for calibration purposes. Settings option 240 may be selected to review or alter the background settings of electronic device 240. Now Playing option 245 may allow the user to review one or more media items, if any, that may be currently playing on electronic device 250.

Figure 3:
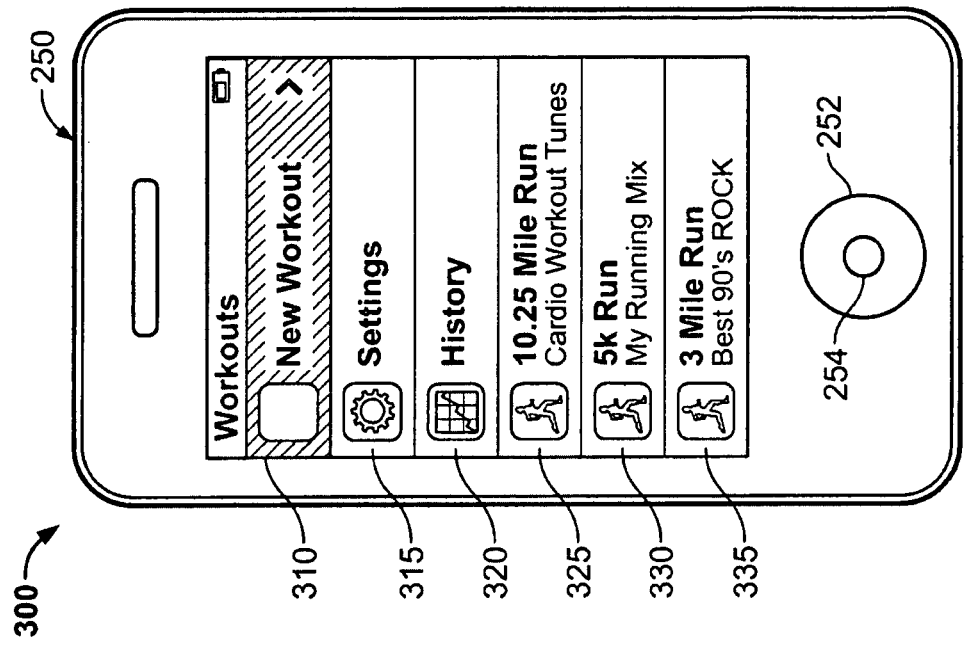
FIG. 3 is a front view of an electronic device with an illustrative display screen for managing workout template options in accordance with some embodiments of the invention.

If a user wants to manage workout templates, the user may access a display screen that permits the user to create, select, review, organize, and upload workout templates stored in electronic device 250, or use the stored workout templates for calibration purposes, using any suitable approach. FIG. 3 is a front view of electronic device 250 with an illustrative display screen 300 for managing workout template options in accordance with some embodiments of the invention. Display screen 300 may be displayed when a user selects Workouts option 235 from display screen 200. Display screen 300 may include several selectable options related to managing workout templates, such as New Workout option 310, Settings option 315, History option 320, template 325 related to a 10.25 mile run workout, template 330 related to a 5 kilometer run workout, template 335 related to a 3 mile run workout, or any other suitable option.

A user of electronic device 250 may select New Workout option 310 to create a new quick start workout template. Settings option 315 may be selected to review workout template settings stored in electronic device 250 and to perform calibration activities. History option 320 may be selected to review, organize, and upload workout template information stored in electronic device 250. Each of templates 325, 330, or 335 may be selected by a user to quick start a previously stored workout template. In some embodiments, templates 325, 330, and/or 335 may be displayed after first selecting History option 320.

Each of templates 325, 330, and 335 may be used with any suitable type of exercise, such as running, machine-based exercise, walking, rowing, or any other suitable type of exercise. In some embodiments, templates 325, 330, and 335 may be used with any suitable combination of types of exercise (e.g., running and weight-lifting for a circuit training workout). Regardless of the type of exercise, each workout template may include any suitable number of workout goals, such as time elapsed, distance traveled, calories burned, desired pace, an activity to be accomplished on an exercise machine, or any other suitable goals to define at least part of the workout template. Each template also may include any suitable media type or types to accompany the selected workout goal or goals, such as music, video, photos, podcasts, a combination of these media types, or any other suitable media type. If the media associated with a template is changed, a new workout template may be created using the same workout goal or goals associated with the changed media. In some embodiments, one or more of workout templates 325, 330, and 335 may not include media.

Each of templates 325, 330, and 335 may represent a repeatable history that may store information gathered from a sensor (e.g., transmitting device 102) during a workout that may be based upon one of templates 325, 330, or 335. Each of templates 325, 330, and 335 may be selected again in the future as a quick start workout option and information from the second workout may also be stored in electronic device 250. For example, a workout template may be accessed again in the future by first selecting Workouts option 235 and then selecting the workout template to quick start the same workout goal with the same associated media, if any.

In some embodiments, in response to a user selecting New Workout option 310, electronic device 250 may determine whether receiver 162 (FIG. 1B) is connected to electronic device 250 or is functioning properly. If receiver 162 is not connected or is not functioning, electronic device 250 may present a message or a display screen (not shown) to the user to indicate that electronic device 250 is waiting for receiver 162 to respond or to be connected. If receiver 162 is functioning, electronic device 250 may determine whether the memory within control circuitry 160 is full, thereby preventing the creation and/or storage of a new workout template in storage component 161. If the memory is full, electronic device 250 may present a message or a display screen (not shown) to the user to indicate that the memory of control circuitry 160 is full and that the memory must be at least partly emptied in any suitable manner (e.g., by removing one or more files or by deleting one or more workouts from the memory) before a new workout template may be created. In some embodiments, electronic device 250 may not determine whether receiver 162 is connected or functioning properly before determining whether the memory in control circuitry 160 is full.

Figures 4, 5:
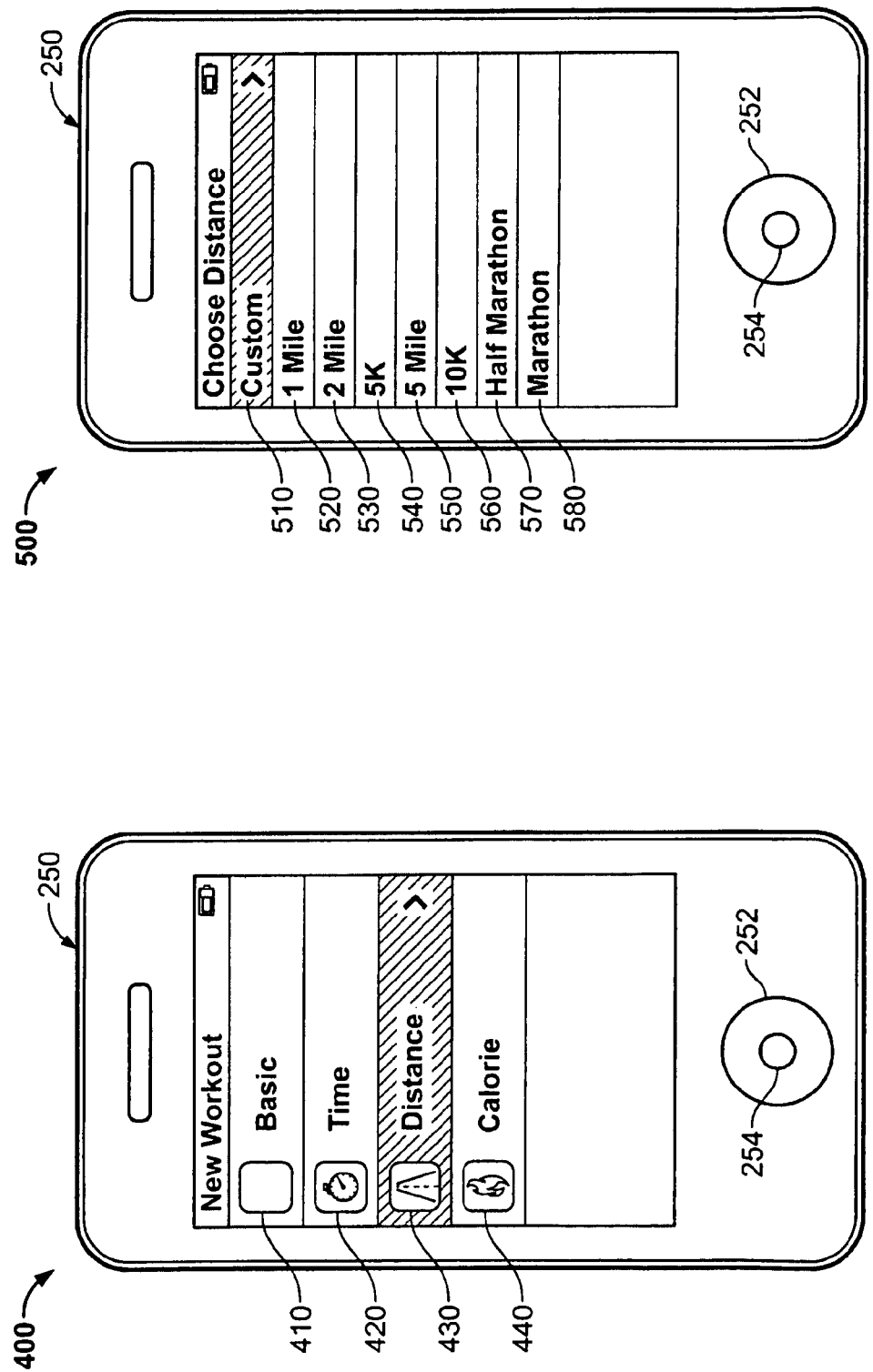
FIG. 4 is a front view of an electronic device with an illustrative display screen for generating a new workout template in accordance with some embodiments of the invention.
FIG. 5 is a front view of an electronic device with an illustrative display screen for defining a workout goal in accordance with some embodiments of the invention.

If a user wishes to create a new workout template, the user may be taken to a display screen that permits the user to create a new workout template that may be stored in electronic device 250 for future quick start selection. FIG. 4 is a front view of electronic device 250 with an illustrative display screen 400 for generating a new workout template in accordance with some embodiments of the invention. Display screen 400 may be displayed when a user selects New Workout option 310 from display screen 300. Display screen 400 may include several options for selecting different workout goals. Options may include, for example, Basic option 410, Time option 420, Distance option 430, Calorie option 440, or any other suitable option. In some embodiments, display screen 400 may also include goal options related to workout pace or a particular activity on an exercise machine (not shown).

A user of electronic device 250 may select Basic option 410 to create a workout template that may not be based upon a particular goal or goals, such as a time goal, a distance goal, a desired pace, an activity on an exercise machine, or a desired number of calories burned. In some embodiments, Basic option 410 may be selected to use electronic device 250 as a stopwatch or a clock to monitor and display in real time the current duration of the workout. A workout template designed using Basic option 410 may include media, as described below with respect to FIG. 7.

A user may select Time option 410 to create a workout template that may be defined at least in part by the desired duration of the user's workout. A user may select Distance option 430 to create a workout template defined at least in part by the distance the user wishes to travel during the workout. Calorie option 440 may be selected to create a workout template defined at least in part by the number of calories the user wishes to burn during the workout. In response to a user selecting Time option 420 or Calorie option 440, the user may be taken to display screens (not shown) that permit the user to create new workout templates based upon default times or calorie amounts or, in some embodiments, custom settings. In some embodiments, in response to a user selecting one of the options of display screen 400, the user may also select another one or more of the options (not shown) to create a workout template based on more than one workout goal. For example, a user may create a workout template based on Distance option 430 (e.g., the user may wish to perform a 10-mile workout) and also based on Time option 410 (e.g., the user may wish to perform the 10-mile workout within 90 minutes).

If a user wishes to define a workout template based upon a desired distance, for example, the user may be taken to a display screen that permits the user to create a new workout template for use with distance workouts using any suitable approach. FIG. 5 is a front view of electronic device 250 with an illustrative display screen 500 for defining a workout goal in accordance with some embodiments of the invention. Display screen 500 may be displayed when a user selects Distance option 430 from display screen 400. Display screen 500 may include several options for selecting different workout goal values. Options may include, for example, Custom option 510, 1 Mile option 520, 2 Mile option 530, 5 Kilometer option 540, 5 Mile option 550, 10 Kilometer option 560, Half Marathon option 570, and Marathon option 580, or any other suitable option.

A user of electronic device 250 may select any of the default distance options 520, 530, 540, 550, 560, 570, or 580 to create a workout template that may be defined at least in part by the user's distance goal for the workout. Alternatively, a user may select Custom option 510 to create a workout template that may be defined at least in part by any suitable unique goal (e.g., a 3.5 mile workout or an 800 meter workout).

Figure 6:
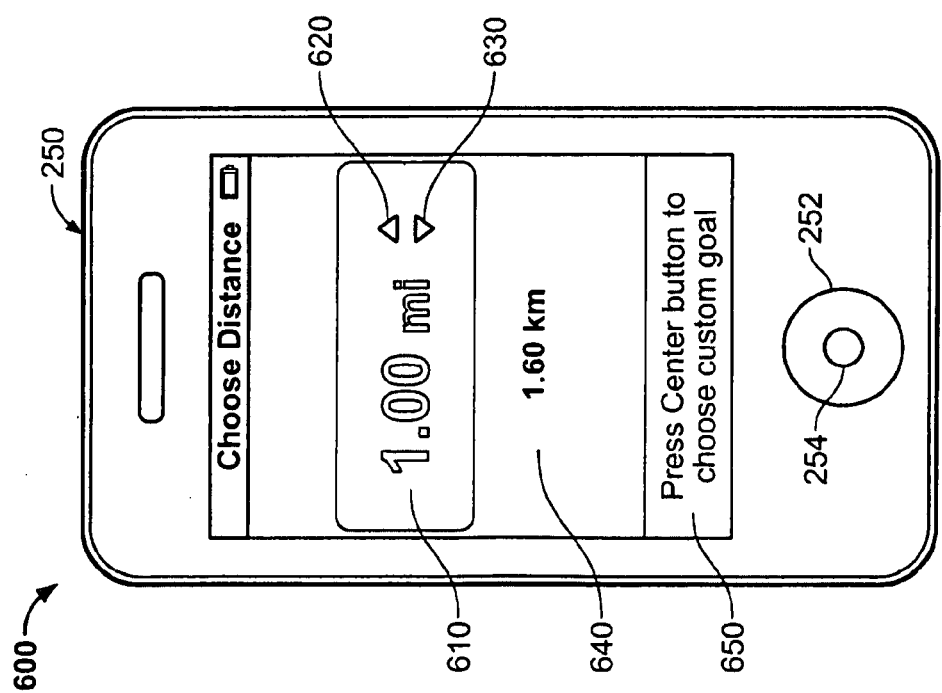
FIG. 6 is a front view of an electronic device with an illustrative display screen for defining a custom goal in accordance with some embodiments of the invention.

If a user wishes to use a custom workout goal, the user may be taken to a display screen that permits the user to create the workout template based upon the custom goal using any suitable approach. FIG. 6 is a front view of electronic device 250 with an illustrative display screen 600 for defining a custom goal in accordance with some embodiments of the invention. Display screen 600 may be displayed when a user selects Custom option 510 from display screen 500. Display screen 600 may include options for defining different custom distances. For example, display screen 600 may display a default distance value which the user may increase or decrease to define the unique distance goal for the workout template. Default distance 610 may be any suitable distance (e.g., one mile). Default distance 610 may be displayed in any suitable units, including, for example, English units, metric units 640, or both. The user of electronic device 250 may increase or decrease default distance 610 using any suitable approach. For example, as shown in FIG. 6, the user may manipulate up arrow 620 using click or scroll wheel 252, button 254, and/or any other suitable input to increase the default distance by any suitable increment (e.g., by tenths of a mile, by quarters of a mile, or by whole miles). Similarly, the user may manipulate down arrow 630 using click or scroll wheel 252, button 254, and/or any other suitable input to decrease the default distance by the same suitable increment. Display screen 600 also may display any suitable message to the user, such as Message 650, to indicate that once the user has defined the unique goal to be applied to the new workout template, the user may confirm the goal by any suitable means (e.g., by pressing button 254 of electronic device 250, by providing a verbal command, or by touching display screen 600). In some embodiments, the user may cancel the selection of a unique distance, or the selection of any workout goal, using any suitable approach. In response to the user cancelling a selection, the user may be returned to a previous display screen.

Figure 7:
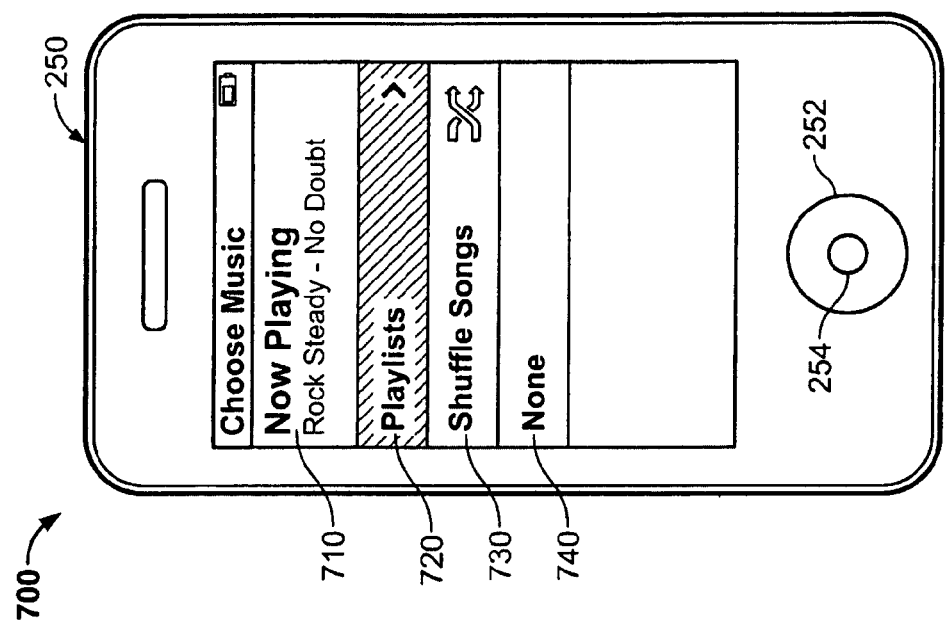
FIG. 7 is a front view of an electronic device with an illustrative display screen for associating media with a workout template in accordance with some embodiments of the invention.

Once the user has selected any suitable number of workout goals (e.g., a default or custom time, distance, calorie amount, pace, or an activity on an exercise machine), the user may be taken to a display screen that permits the user to associate any suitable media with the selected workout goal using any suitable approach. FIG. 7 is a front view of electronic device 250 with an illustrative display screen 700 for associating media with a workout template in accordance with some embodiments of the invention. Display screen 700 may be displayed when a user has selected at least one workout goal (e.g., using display screen 600) and desires to associate media with the workout goal or goals to complete the definition of the workout template. Display screen 700 may include Now Playing item 710 that may display any suitable media item or items currently being played back by electronic device 250 while the user navigates display screen 700. Display screen 700 may also include any suitable options for selecting one or more media items to associate with the previously selected workout goal or goals. For example, display screen 700 may include Playlists option 720, Shuffle Songs option 730, and None option 740.

A user may select Playlists option 720 to be taken to a subsequent display screen that may present any suitable number of media playlists to associate with the workout goal or goals. Each media playlist may include any suitable number of media items of any suitable media type, including music, videos, photographs, podcasts, other audio or video files, or any other suitable media types or combinations of media types. Shuffle Songs option 730 may be selected to alter the order in which media may be played back on electronic device 250. For example, a user may allow all of the media items stored within electronic device 250 to be played back as part of the workout template. The user may shuffle the order in which those media items may be played back by selecting Shuffle Songs option 730. It is to be understood that option 730 may be used with any suitable media type, and is not limited to shuffling music media items. None option 740 may be selected by a user to define a workout template that does not include at least one associated media item (e.g., the workout template is defined as the selected workout goal or goals).

In some embodiments, Shuffle Songs option 730 may be selected to alter the order in which media items within a particular playlist associated with a workout template may be played back by electronic device 250 during a workout. For example, a previously stored workout template may or may not lead to the generation of a new workout template if the media associated with the previously stored workout goal or goals is altered. The media associated with the previously stored workout template may be altered if Shuffle Songs option 730 is selected to reorganize the playback of media items associated with the workout goal or goals. The associated media may also be altered, and thus a new workout template may be created, by associating different media, or by forgoing the use of any media, with the previously stored workout goal or goals.

In some embodiments, while a user may be navigating display screen 700, electronic device 250 may determine whether a sensor (e.g., transmitting device 102, FIG. 1A) is linked (not shown) to electronic device 250. The linked sensor may be used in conjunction with a workout template during a workout to provide signal information that may be used to generate workout statistics. If a sensor has not been detected by or linked to electronic device 250, electronic device 250 may communicate to the user in any suitable manner the lack of connection (e.g., by displaying a message such as "Not Linked to Sensor," or "Walk around to activate sensor," if the sensor has been detected but has not communicated with electronic device 250).

Figure 8:
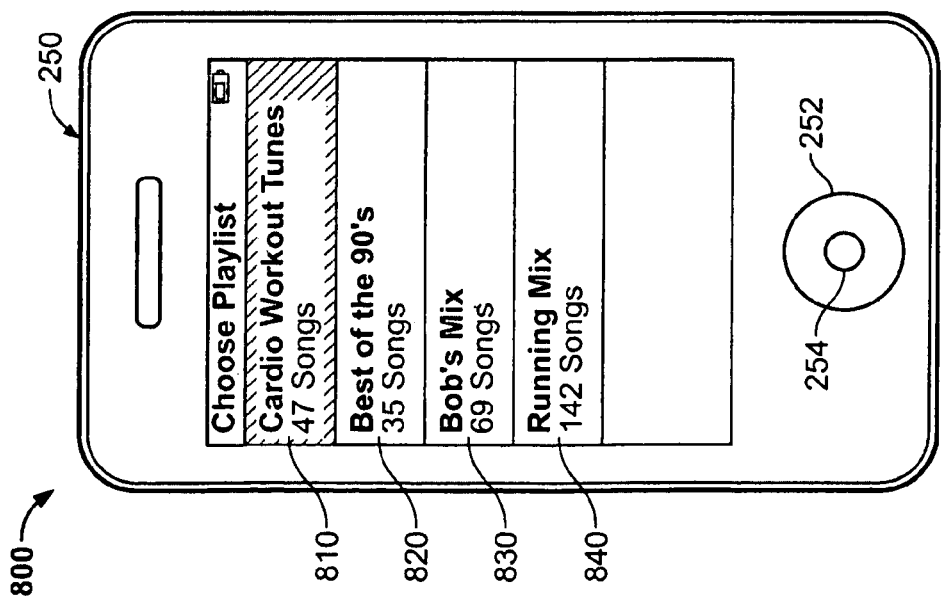
FIG. 8 is a front view of an electronic device with an illustrative display screen for selecting one or more media playlists in accordance with some embodiments of the invention.

If a user wishes to associate a playlist with the previously selected workout goal or goals, the user may be taken to a display screen that permits the user to associate at least one media item with the new workout template using any suitable approach. FIG. 8 is a front view of electronic device 250 with an illustrative display screen 800 for selecting one or more media playlists in accordance with some embodiments of the invention. Display screen 800 may be displayed when a user selects Playlists option 720 from display screen 700. Display screen 800 may display any suitable number of media playlists that a user may select for association with the workout goal or goals. For example, display screen 800 may display playlists 810, 820, 830, and 840. Each of playlists 810, 820, 830, and 840 may have a unique title and may indicate the number and/or the type of media items compiled within each playlist. In some embodiments, playlists 810, 820, 830, and/or 840 may include any suitable combination of media types. In some embodiments, display screen 800 may include a list of media items organized in any suitable fashion rather than a list of media playlists that may represent compilations of media items. The user may select any suitable number of individual media items to associate with the workout goal or goals.

Playlists or individual media items may be presented on display screen 800 in any suitable order, such as in alphabetical order, in order of predominant media type, in forward or reverse chronological order of date compiled or date stored in electronic device 250, in order of the user's preference (e.g., the most frequently selected playlists or media items may appear first on display screen 800), in order of mood types that may be associated with a particular playlist or media item, or in any other suitable order. In some embodiments, a user may cancel a selection of a media playlist of at least one media item and may be returned to a previous display screen using any suitable method, for example by selecting a "Cancel" option (not shown).

Figure 9:
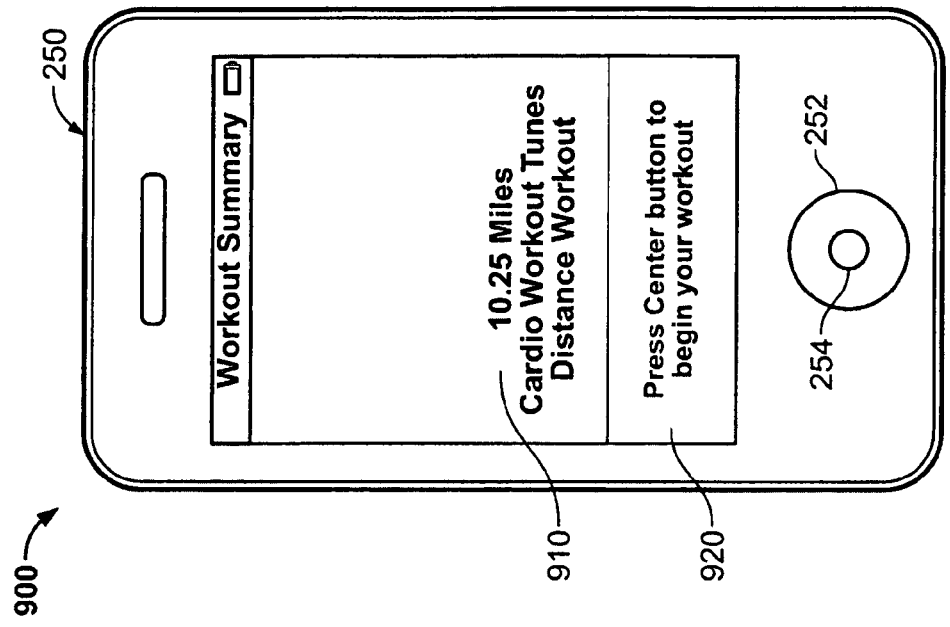
FIG. 9 is a front view of an electronic device with an illustrative display screen for summarizing a new workout template in accordance with some embodiments of the invention.

Once a user selects any suitable media (e.g., playlist 810) to associate with the workout goal or goals, or chooses not to associate media, the user may be taken to a display screen that permits the user to review the newly defined workout template using any suitable approach. The new workout template may be stored in electronic device 250 for future quick start selection. FIG. 9 is a front view of electronic device 250 with an illustrative display screen 900 for summarizing a new workout template in accordance with some embodiments of the invention. Display screen 900 may be displayed when a user creates a new workout template using display screens 200-800. Display screen 900 may display any suitable information to permit a user to review the newly defined workout template. For example, display screen 900 may display summary 910 of the new workout template, which may include any suitable number of workout goals (e.g., a custom distance of 10.25 miles) and associated media (e.g., a media playlist entitled "Cardio Workout Tunes"). In some embodiments, display screen 900 may include any suitable method of returning to any of display screens 200-800 to change the selected workout goal or goals and/or the associated media, such as a "Change" option (not shown). Once the user is satisfied with the selection of the workout goals and/or any associated media, electronic device 250 may store the new workout template. The new workout template may be selected in the future to quick start another workout based on the same workout goal or goals and the same associated media.

Display screen 900 may also include any suitable message, such as Message 920, that may guide the user in starting a workout on electronic device 250 using the new workout template (e.g., display screen 900 may instruct the user to "Press Center button to begin your workout" using the new workout template). In some embodiments, a workout may be started using the new workout template in any suitable fashion. For example, the workout may start when the user provides a verbal command, depresses click or scroll wheel 252 or button 254, or touches display screen 900. In some embodiments (not shown), the workout may be started when the user starts moving in any suitable manner that may permit electronic device 250 to start a clock or start tracking a distance traveled, a number of calories burned, or an activity on an exercise machine. Once the user begins a workout on electronic device 250 using the new workout template, the sensor may transmit signals containing workout information that electronic device 250 may store as workout statistics (e.g., distance traveled, time elapsed, number of calories burned, or pace or activity achieved).

In some embodiments, while a user is reviewing display screen 900, electronic device 250 may determine (not shown) whether a battery or other power source is available to power a sensor (e.g., transmitting device 102) during the duration of a workout based on the new workout template. In response to electronic device 250 determining that a power source is not available or is insufficient to power the sensor during the workout, electronic device 250 may display any suitable message, such as "Sensor Battery Low—Replace Sensor Soon," to indicate a need for sufficient power.

Figure 10:
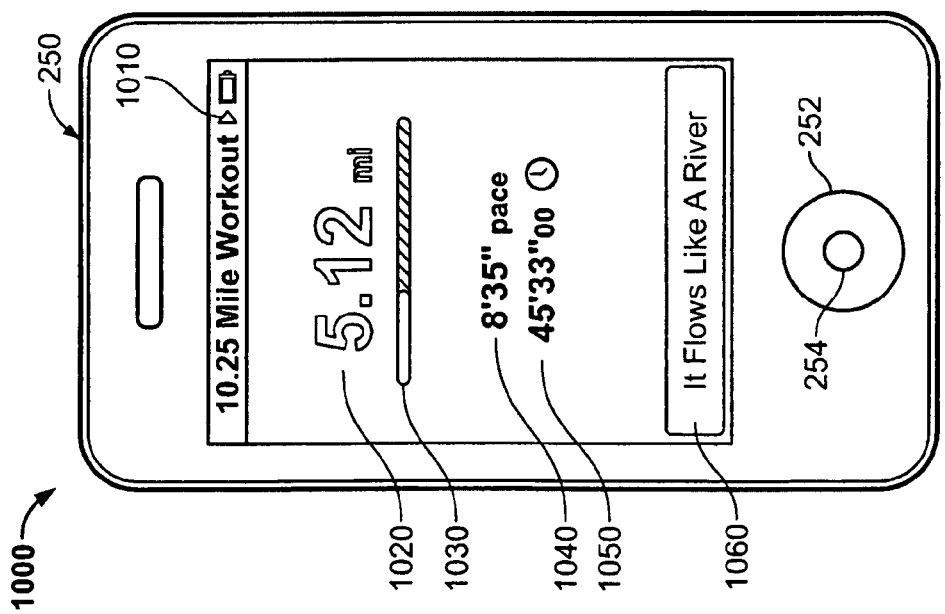
FIG. 10 is a front view of an electronic device with an illustrative display screen for monitoring a workout in accordance with some embodiments of the invention.

In response to a user selecting Message 920 or otherwise beginning a workout using the newly defined workout template, the user may be taken to a display screen that permits the user to monitor the workout using any suitable approach. Workout statistics generated from the workout may be stored in electronic device 250 (e.g., in storage component 161) for future review and for uploading purposes. FIG. 10 is a front view of electronic device 250 with an illustrative display screen 1000 for monitoring a workout in accordance with some embodiments of the invention. Display screen 1000 may be displayed during a user's workout that may be based at least in part on the new workout template defined using display screens 200-900.

Display screen 1000 may display any suitable information to permit a user to monitor the progress of an ongoing workout using a workout template. For example, display screen 1000 may include Status indicator 1010 to indicate that the workout template is currently operating, or alternatively to indicate that media associated with the workout template is currently playing. Distance traveled option 1020 may indicate the distance covered by the user since the beginning of the workout. For example, the sensor (e.g., transmitting device 102) may send signals to electronic device 250 containing information related to how far the user has traveled since the workout began. Progress bar 1030 may display the relative completion of the user's workout based upon the workout goal defined within the workout template. Alternatively, progress bar 1030 may display the relative completion of the current media item being played back on electronic device 250. Pace indicator 1040 may indicate the user's pace (e.g., running pace), if relevant, during the workout. Time elapsed indicator 1050 may indicate the ongoing length of the current workout. In some embodiments, if a user has associated media with the workout template, Media indicator 1060 may display the media item or the playlist currently being played back by electronic device 250 as part of the workout.

In some embodiments, these options may be oriented such that display screen 1000 may display instead a time elapsed, a number of calories burned, a pace maintained, or an exercise machine being used as the primary information near the top of display screen 1000.

In some embodiments, a user may designate any suitable number of media items (e.g., a song, a video, a photograph) as "PowerMedia" items, which the user may select for playback at any time during any workout. A PowerMedia item may be part of any suitable playlist associated with a workout template, or it may be associated with a workout template as an individual media item. The PowerMedia item may be played back by electronic device 250 during a workout regardless of what workout template is currently being used or regardless of when the PowerMedia item may be selected during the workout.

For example, Message 1060 may indicate what media item is currently playing during the workout. A user may wish to receive extra motivation during the workout using a pre-selected PowerMedia item. The user may provide any suitable input (e.g., providing an extended press to button 254) to direct electronic device 250 to override the playback of the current media item and to begin playback of the pre-selected PowerMedia item. The PowerMedia item may be shown in place of the current media item in Message 1060. Once playback of the PowerMedia item is completed, the user may choose to play back the PowerMedia item again, or the user may choose to continue playback of the interrupted media item or any other media item or playlist associated with the current workout template.

In some embodiments, a workout template may be created after the user has completed a workout. For example, a user may wish to use electronic device 250 in conjunction with a workout (e.g., a 10 mile run). Electronic device 250 may receive workout-related information during the workout from a sensor (e.g., transmitting device 102) and may store workout statistics generated from the information. The user may also select one or more media items or playlists to accompany the workout. When the workout is completed or has been finished otherwise, electronic device 250 may permit the user to create a workout template using the 10 mile run as the workout goal and the media that may have accompanied the run. For example, when the workout is complete, electronic device 250 may display a display screen to the user (not shown), permitting the user to save the workout goal or goals and the associated media together as a new workout template for quick start selection in the future. Alternatively, the user may choose not to create a workout template and electronic device 250 may save the workout statistics or may delete the statistics.

Figure 11:
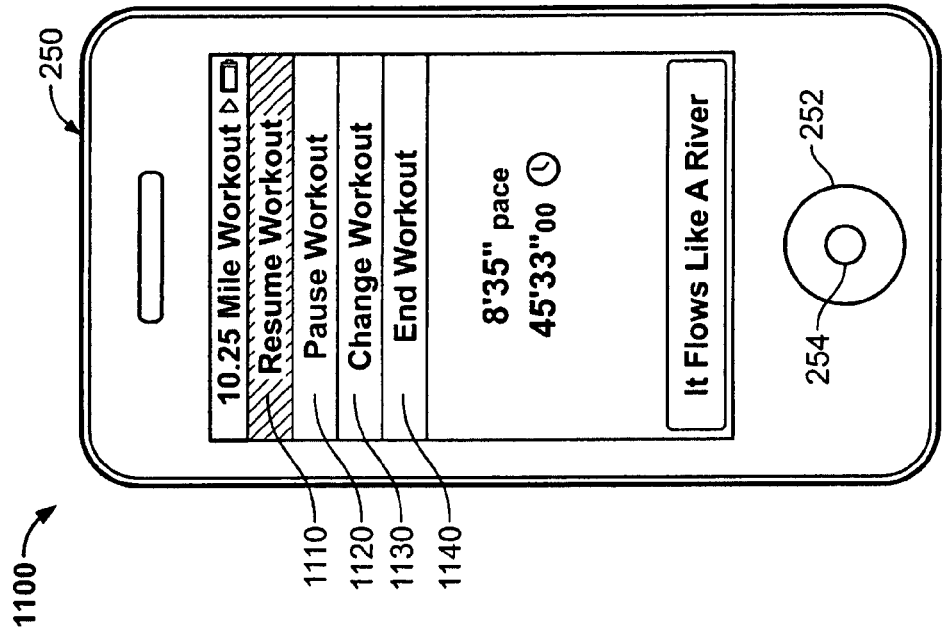
FIG. 11 is a front view of an electronic device with an illustrative display screen for viewing a workout menu in accordance with some embodiments of the invention.

In some embodiments, the user may stop the playback of media during a workout, or stop, alter, or pause the workout. FIG. 11 is a front view of electronic device 250 with an illustrative display screen 1100 for viewing a workout menu in accordance with some embodiments of the invention.

Display screen 1100 may be displayed during a workout that may be based at least in part on a workout template. Display screen 1100 may be displayed or superimposed over any suitable display screen, such as display screen 1000, using any suitable method (e.g., in response to the user pressing click or scroll wheel 252 or button 254, or automatically by electronic device 250 in response to the workout being stopped). Display screen 1100 may include any suitable menu options including, for example, Resume Workout option 1110, Pause Workout option 1120, Change Workout option 1130, End Workout option 1140, and any other suitable option. The menu options of display screen 1100 may depend on the context in which the menu is requested by the user (e.g., during a workout), as described more fully in a U.S. Patent Application titled "Contextual Menus In An Electronic Device," filed concurrently herewith, which is incorporated by reference herein in its entirety.

A user may select Resume Workout option 1110 to return to a previous display screen, such as display screen 1000, to continue monitoring an ongoing workout. A user may select Pause Workout option 1120 to return to a previous display screen 1000, but the workout may not continue and workout information sent from the sensor may not be stored by electronic device 250 in storage component 161 until the user chooses to resume or end the workout. In response to a user selecting Change Workout option 1130 to select a different workout template or to create a new workout template, electronic device 250 may display screens similar to display screen 300 to select a previously stored workout template or similar to display screens 400-800 to create a new workout template. In response to a user selecting End Workout option 1140, the current workout may be completed and statistics related to the workout may be summarized for the user's review.

In some embodiments, electronic device 250 may monitor its communication with the sensor during the workout. If the sensor does not communicate with electronic device 250 for a defined time period, electronic device 250 may pause the ongoing workout and may notify the user accordingly.

In response to a user selecting End Workout option 1140, the user may be taken to a display screen that permits the user to review a summary of statistics from the completed workout using any suitable method. FIG. 12 is a front view of electronic device 250 with an illustrative display screen 1200 for viewing a workout summary in accordance with some embodiments of the invention. Display screen 1200 may be displayed in response to a user completing a workout or otherwise ending a workout. In some embodiments, display screen 1200 may display any suitable information to permit a user to review a workout that may be based at least in part on a workout template. For example, display screen 1200 may include workout title 1210. Workout title 1210 may include the name of the workout template that was used during the workout and may include the date on which the workout ended. In some embodiments, workout title 1210 may appear on display screen 2100 as a previous workout that the user may select in the future for review and uploading purposes.

Display screen 1200 also may include any suitable workout statistics. For example, display screen 1200 may include elapsed time 1220, workout pace 1230, distance traveled 1240, calories burned 1250, associated media 1260, and any other suitable statistics or information, such as an activity performed on an exercise machine (not shown). The workout statistics may be generated by electronic device 250 using signal information received from the sensor and may be stored in electronic device 250 with respect to the particular workout. The user may review these statistics in the future, or may compare these statistics to statistics related to another prior workout stored within electronic device 250. The user may also designate which statistics to gather with respect to a particular workout, which may depend at least in part on how the workout template underlying the workout may be defined, and the designation may be stored in electronic device 250. In some embodiments, the statistics may be transmitted (e.g., uploaded) to a remote source for sharing with other users.

In some embodiments, a completed workout may be used to calibrate electronic device 250 with respect to a particular sensor using any suitable method. FIG. 13A is a front view of electronic device 250 with an illustrative display screen 1300 for calibrating electronic device 250 in accordance with some embodiments of the invention. Display screen 1300 may be displayed in response to electronic device 250 determining that a completed or otherwise ended workout may be used to calibrate electronic device 250 with respect to a particular sensor (e.g., transmitting device 102). For example, the user may complete a workout and may be shown display screen 1200, which may include statistics related to the workout. After reviewing the statistics, the user may realize that one or more of the reported statistics is incorrect. The user may provide any suitable input (e.g., an extended press of button 254) to electronic device 250, causing electronic device 250 to analyze whether the completed workout may be used to calibrate electronic device 250.

If electronic device 250 determines that the workout may be used for calibration purposes, display screen 1300 may provide any suitable options for calibrating electronic device 250. For example, display screen 1300 may include Message 1310 indicating to the user that the workout from display screen 1200 may be used to calibrate electronic device 250 with respect to the linked sensor that may have transmitted the workout information to electronic device 250. Message 1310 may also instruct the user on how to calibrate electronic device 250 if one or more of the reported workout statistics (e.g., distance traveled 1240) was incorrect. A user may select Calibrate option 1320 to calibrate electronic device 250 if one or more of the workout statistics shown in display screen 1200 was incorrect. A user may select Cancel option 1330 if the user does not wish to calibrate electronic device 250 using the completed workout.

Figure 13B:
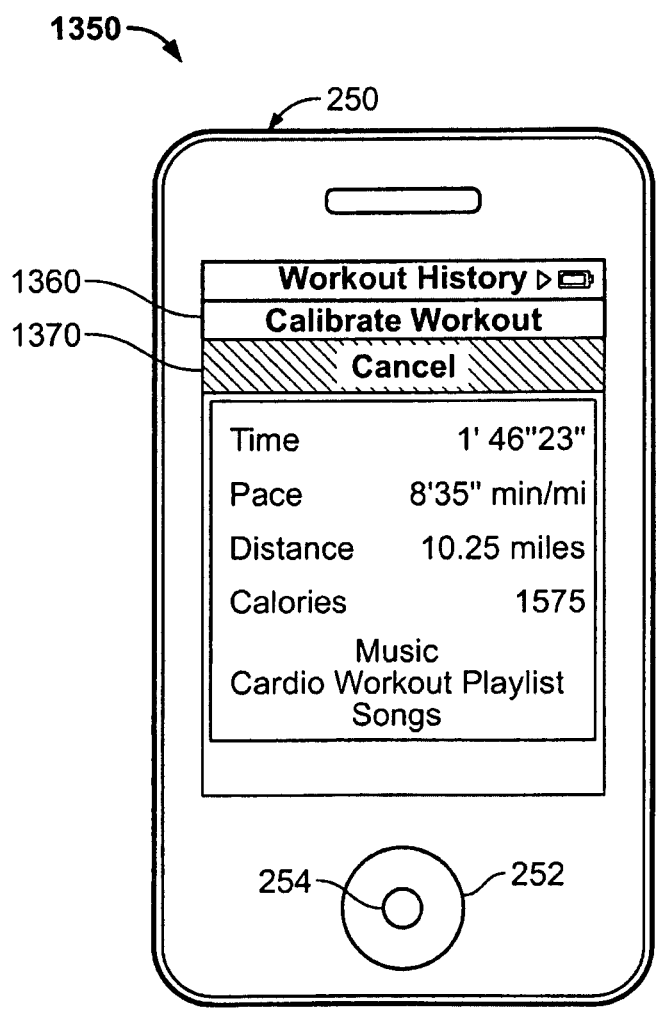
FIG. 13B is a front view of an electronic device with an alternative illustrative display screen for calibrating an electronic device in accordance with some embodiments of the invention.

FIG. 13B is a front view of an electronic device with an alternative illustrative display screen 1350 for calibrating electronic device 250 in accordance with some embodiments of the invention. In some embodiments, display screen 1350 may be displayed instead of display screen 1300 in response to a user deciding to calibrate electronic device 250 with respect to a particular sensor (e.g., transmitting device 102). For example, the user may complete a workout and may be shown display screen 1200, including workout statistics. If one or more of the reported statistics is incorrect, the user may provide any suitable input to electronic device 250, causing electronic device 250 to present display screen 1350. Display screen 1350 may be displayed or superimposed over any suitable display screen, such as display screen 1200, using any suitable method (e.g., in response to the user pressing click or scroll wheel 252 or button 254, or automatically by electronic device 250 in response to the workout being stopped).

Display screen 1350 may include any suitable menu options including, for example, Calibrate Workout option 1360, Cancel option 1370, and any other suitable option. As with display screen 1100, the menu options of display screen 1350 may depend on the context in which the menu is requested by the user. A user may select Calibrate Workout option 1360 to be taken to a subsequent display screen that may permit a calibration of electronic device 250 to be performed with respect to the one or more incorrect statistics. In response to a user selecting Cancel option 1370, the user may be returned to display screen 1300 and the current workout may continue or be completed.

If a user wishes to calibrate electronic device 250, the user may be taken to a display screen to define the calibration using the workout using any suitable method. FIG. 14 is a front view of electronic device 250 with an illustrative display screen 1400 for defining a calibration in accordance with some embodiments of the invention. Display screen 1400 may be displayed in response to a user electing to calibrate electronic device 250 using the workout (e.g., by selecting Calibrate option 1320 in FIG. 13A or Calibrate Workout option 1360 in FIG. 13B). Display screen 1400 may include any suitable options for defining the calibration of electronic device 250 using the workout. For example, display screen 1400 may include actual value 1410 that the user may adjust to define the calibration. Actual value 1410 may be in units of distance, indicating that the calibration may alter how electronic device 250 generates distance statistics using signal information received from the sensor. In some embodiments, actual value 1410 may include any suitable units by which to define the calibration, such as time, pace, calories, or any other suitable unit.

Actual value 1410 may be compared to recorded value 1420, which may be in the same units as actual value 1410 (e.g., distance). Recorded value 1420 may represent the value of the statistic generated by electronic device 250 during the workout using information transmitted from the sensor. If recorded value 1420 is incorrect, the user may increase actual value 1410 by manipulating up arrow 1430 (e.g., using click or scroll wheel 252 and/or button 254), or may decrease actual value 1410 by manipulating down arrow 1440, until actual value 1410 reflects the correct distance traveled during the workout. The correct distance may or may not equal recorded value 1420.

Once the user has finished adjusting actual value 1410, the user may complete the calibration using any suitable method. For example, Message 1450 may instruct the user to press the Center button (e.g., button 254) of electronic device 250 to record actual value 1410 as the distance traveled during the workout shown on display screen 1200. Actual value 1410 may thereafter be included in the workout statistics shown in display screen 1200. Electronic device 250 may also use actual value 1410 to calibrate how it generates the calibrated statistic (e.g., distance traveled) in the future using workout-related information from the linked sensor. Upon following the instructions of Message 1450, the user may be returned to any suitable display screen, such as the workout summary shown on display screen 1200.

If, instead of selecting New Workout option 310 (FIG. 3) to create a new workout template, a user wishes to review or alter workout-related settings stored in electronic device 250, the user may select Settings option 315 and may be taken to one or more subsequent display screens (not shown) that permit the user to review, select, and organize those stored settings and perform calibrations using any suitable approach.

In some embodiments (not shown), the electronic device may perform a calibration or recalibration with respect to any type of movement that may be calibrated on the electronic device, as described more fully in U.S. Patent Publication No. 2007/0271065, published Nov. 22, 2007, entitled "Portable Media Device With Workout Support," and as described more fully in U.S. Patent Publication No. 2007/0270721, published Nov. 22, 2007, entitled "Calibration Techniques For Activity Sensing Devices," each of which is incorporated by reference herein in its entirety. In some embodiments (not shown), the user may associate at least one media item with a calibration exercise (e.g., the movement, such as running or walking, to be calibrated) and may review a calibration template that includes the calibration exercise and the associated media. In response to the user confirming the settings of the calibration template, the electronic device may perform the calibration using the calibration template. Information generated from the calibration may be stored in electronic device 250 for future application with suitable workout templates and the linked sensor.

In some embodiments, electronic device 250 may analyze whether the pace of the calibration was too inconsistent to calibrate electronic device 250 with respect to the calibration exercise. If the pace was too inconsistent, electronic device 250 may present, for example, a subsequent display screen to the user (not shown), to indicate that the pacing of the calibration was too inconsistent to obtain an accurate reading (e.g., the user may be directed to "Press Center button to try again" and/or "Press Menu to cancel"). In some embodiments, electronic device 250 may analyze whether the distance traveled during the calibration was incorrect. If the distance traveled was incorrect in light of how the calibration template was defined, electronic device 250 may present a subsequent display screen to the user (not shown) to indicate that the traveled distance did not match the calibration goal (e.g., the user may be directed to "Press Center button to try again" and/or "Press menu to cancel").

In some embodiments, the user may also review, select, and organize stored workout-related settings (not shown) using any suitable approach. For example, a user may choose a PowerMedia option to select or unselect certain media items, which may be associated with one or more workout templates, as PowerMedia items. A user may select a spoken feedback option to arrange for any suitable type of feedback (e.g., audio feedback, visual feedback, or a combination of audio and visual feedback) from electronic device 250 during a workout. A distances option may be selected to review and/or alter the list of default distances offered by display screen 500 (FIG. 5). A weight option may be selected to review and/or alter the user's weight as stored in electronic device 250. The user's weight may be used by electronic device 250 with workout templates, for example, in which information such as calories burned may be desired. A remote option may be selected to review and/or alter settings related to using a remote control to operate electronic device 250 during a workout. In some embodiments, in response to selecting the remote option, electronic device 250 may proceed to establish or terminate a link with the remote control. If the link is terminated, electronic device 250 may ignore signals from the remote control until the link is reestablished. A screen orientation option may be selected to review and/or alter settings related to how any display screen may appear on electronic device 250.

In some embodiments, a sensor option (not shown) may enable the user to either establish a link with a sensor (e.g., transmitting device 102) or have electronic device 250 perform a calibration using a calibration template as described above. If electronic device 250 is unable to detect the presence of the sensor, for example if receiver 162 (FIG. 1B) is not connected to electronic device 250 or is not functioning properly within control circuitry 160 to detect the sensor, electronic device 250 may display any suitable message to notify the user that receiver 162 is not connected, such as "Waiting for Receiver," and/or "Attach a receiver to begin a workout" (not shown).

A user may select a link option to create a link (e.g., communication path 140, FIG. 1A) between receiver 162 and the sensor (e.g., transmitting device 102). The link may be used during a workout to transmit information about the user's movement from the sensor to electronic device 250 for processing and for storage in storage component 161. The link may also be established by electronic device 250 for calibration purposes with respect to a particular sensor. If electronic device 250 and the sensor are linked via receiver 162, the user may receive any suitable message to instruct the user to activate the sensor, such as "Searching for sensor . . . walk around to activate the new sensor" (not shown). If receiver 162 and the sensor have already been linked, the user may first receive a message that electronic device 250 is already linked with the sensor. If the sensor functions properly and the link is properly established, the user may receive any suitable message from electronic device 250 that the user may proceed with a workout such as "Press the Center button to continue." If more than one sensor is detected by electronic device 250, the user may receive a message that the user should move away from all other sensors to establish a proper link with the appropriate sensor. If the sensor cannot be found despite the proper functioning of receiver 162, the user may receive any suitable message, such as "Press the Center button to continue searching" to indicate that a proper link has not yet been established with the sensor.

If, instead of selecting New Workout option 310 (FIG. 3) or Settings option 315, the user wishes to review prior workouts and related statistics, the user may be taken to a display screen that permits the user to review the prior workouts using any suitable approach. FIG. 15 is a front view of electronic device 250 with an illustrative display screen 2100 for selecting a workout history in accordance with some embodiments of the invention. Display screen 2100 may be displayed in response to a user selecting History option 320 from FIG. 3. Display screen 2100 may display any suitable options to permit a user to review previously completed workouts and statistics related to the workouts. For example, display screen 2100 may include Workout Totals option 2110, Personal Bests option 2120, a series of workouts 2130, 2140, 2150, and 2160, each of which may be related to an individual prior workout, and other suitable options.

If a user wishes to review information related to all prior workouts that may be stored in electronic device 250, the user may be taken to a display screen to review accumulated workout statistics using any suitable method. FIG. 16 is a front view of electronic device 250 with an illustrative display screen 2200 for reviewing a summary of workouts in accordance with some embodiments of the invention. Display screen 2200 may be displayed in response to a user selecting Workout Totals option 2110 from FIG. 15. Display screen

2200 may display any suitable options to permit a user to review combined statistics related to all of the workouts that may be stored in electronic device 250 (e.g., stored in storage component 161). For example, display screen 2200 may include workouts statistic 2210, which may report the number of workouts, whether or not completed, stored in electronic device 250. Display screen 2200 may include farthest statistic 2220, which may report the farthest distance traveled with respect to one stored workout. Run distance statistic 2230 may report the distance traveled by the user after combining all of the recorded distances from each of the stored workouts, if appropriate. Time statistic 2240 may report the combined elapsed time of all of the stored workouts, and calories statistic 2250 may report the combined number of calories burned in relation to all of the stored workouts. In some embodiments, display screen 2200 may also include any other suitable information (not shown), such as the number of times the user performed an activity on a particular exercise machine, the duration of the longest workout stored in electronic device 250, the average pace achieved by the user in one or more of the stored workouts, and any other suitable information.

In some embodiments, a user may delete from electronic device 250 all of the workouts that may be used to compile the statistics for display screen 2200 using any suitable method. For example, the user may provide any suitable input to electronic device 250 (e.g., an extended press of button 254) and the user may be taken to a subsequent contextual menu that may be overlaid over display screen 2200 (not shown), similar to the manner in which display screen 1100 and/or display screen 1350 may be overlaid over another display screen. The menu may offer the user any suitable options, including an option to clear all of the workouts stored in electronic device 250, and an option to cancel the process.

If a user wishes to review information related to workout achievements, the user may be taken to a display screen to review personal best statistics. FIG. 17 is a front view of electronic device 250 with an illustrative display screen 2300 for reviewing a summary of workout achievements in accordance with some embodiments of the invention. Display screen 2300 may be displayed in response to a user selecting Personal Bests option 2120 from FIG. 15. Display screen 2300 may permit a user to review particular achievements, or "bests," assembled from all of the workouts that may be stored in electronic device 250. For example, display screen 2300 may include any suitable number of entries. Each entry 2310, 2320, 2330, 2340, 2350, 2360, 2370, 2380, and 2390 may be associated with a particular workout goal or goals, including custom workout goals, such as a distance (e.g., 1 kilometer in entry 2310, 1 mile in entry 2350). Display screen 2300 may display a best value related to each entry (e.g., 5 minutes, 33 seconds for entry 2310, or 7 minutes, 44 seconds for entry 2350). The best value may include any suitable units. In some embodiments, the best value may correspond to the maximum number of calories burned in one workout for a given entry, such as the greatest amount of calories burned during 10 kilometer run entry 2340. In some embodiments, the best value may correspond to the best pace set in one workout for a given entry, such as the fastest pace run by the user during 5 mile run entry 2370. If the user has no personal best value for a given entry (e.g., entry 2380), display screen 2300 may leave the best value blank or may indicate that no value exists using any suitable method.

If a user wishes to review statistics related to a particular workout, the user may be taken to a display screen similar to display screen 1200 (FIG. 12) to review statistics compiled during the workout using any suitable method. For example, a user may select workout 2130, and the user may be taken to a subsequent display screen (not shown) that may display any suitable statistics related to workout 2130, such as the time taken to complete workout 2130, the pace, the distance traveled, and/or the calories burned during workout 2130. If media was associated with workout 2130, that media may also be displayed. In some embodiments, a user may delete workout 2130 from electronic device 250 using any suitable method. For example, the user may provide any suitable input to electronic device 250 (e.g., an extended press of button 254) and the user may be taken to a subsequent contextual menu (not shown) that may be overlaid over the display of workout 2130, similar to the manner in which display screen 1100 and/or display screen 1350 may be overlaid over another display screen. The menu may offer the user any suitable options, including an option to delete workout 2130, and an option to cancel the process.

In some embodiments, the user may have the option of quick starting workout 2130 again from display screen 2100 by selecting workout 2130 (e.g., a subsequent menu may appear in response to selecting workout 2130 from display screen 2100, giving the user the alternative of quick starting workout 2130 or viewing previous statistics gathered during workout 2130). Alternatively, the user may quick start workout 2130 again after reviewing previous statistics related to workout 2130, as described above.

Figure 18:
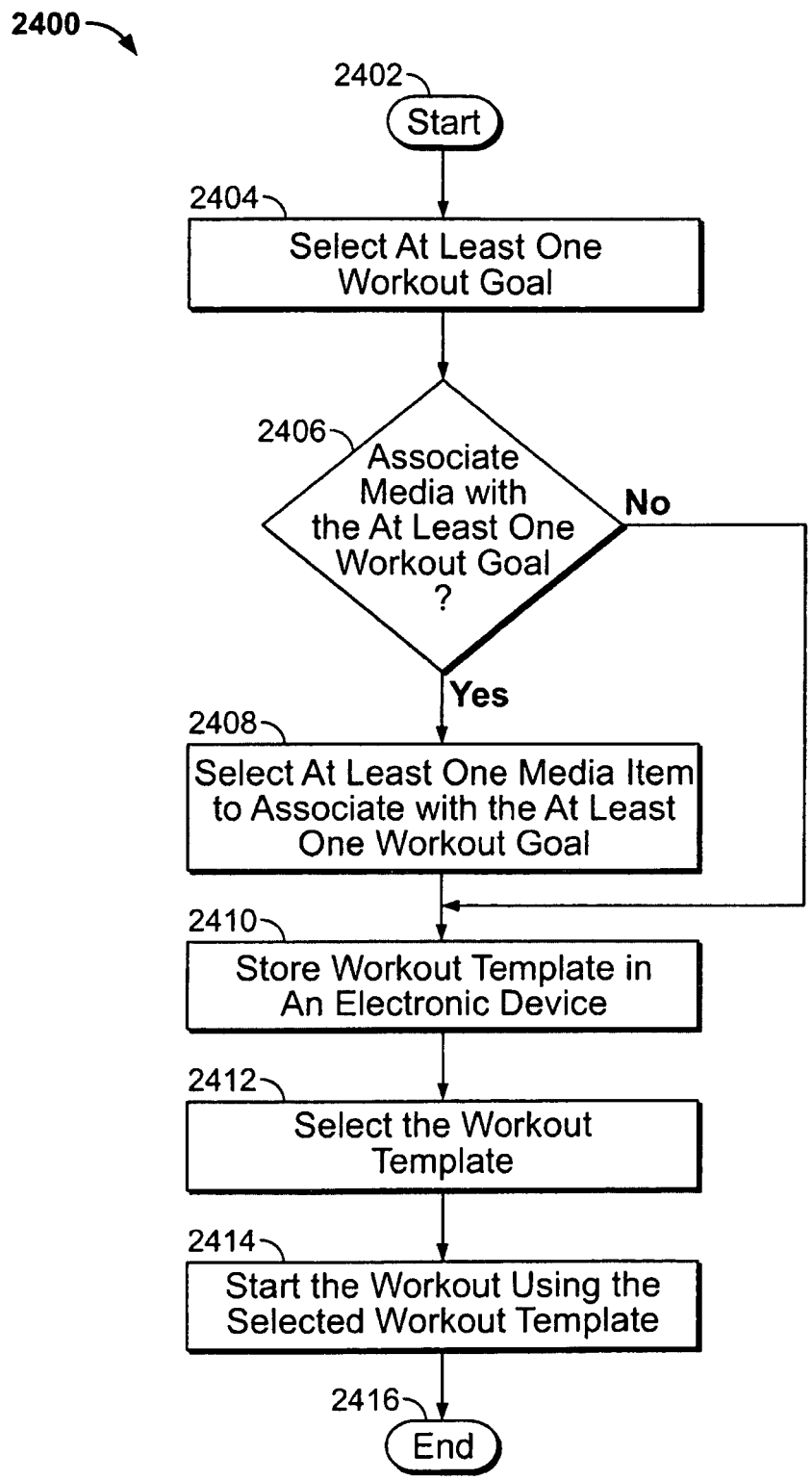
FIG. 18 is a flowchart of an illustrative process for performing a workout in accordance with some embodiments of the invention.

FIG. 18 is a flowchart of an illustrative process for performing a workout in accordance with some embodiments of the invention. Process 2400 may begin at step 2402. At step 2404, a user may select any suitable number of workout goals as part of defining a workout template. For example, a user may wish to run as a workout, and the workout goal may be a specific distance that the user may wish to run during the workout. The workout goal or goals may include a default value stored in an electronic device (e.g., electronic device 250) or one or more of the selected workout goals may have a custom value.

Process 2400 may advance to step 2406, in which the user may determine whether to associate any media (e.g., music, video, photographs, podcasts, other audio or visual media, or any other suitable media or combination therein) with the selected workout goal or goals. If the user wishes to associate at least one media item, process 2400 may advance to step 2408 where the user selects at least one media item to associate with one or more of the workout goals. In response to the user selecting at least one associated media item, process 2400 may advance to step 2410 in which the workout template, including the defined workout goal or goals and the associated media, may be stored in the electronic device (e.g., in storage component 161). If the user decides not to associate media with one or more of the workout goals at step 2406, process 2400 may still advance to step 2410 where the workout goal or goals may be stored as the workout template.

Process 2400 may advance to step 2412, where the workout template may be selected using any suitable approach, including for example, by a press of a click or scroll wheel or a button, a verbal command, a touch, or any other suitable approach. At step 2414, the user may start a workout using the workout template selected in step 2412. The workout may be started using any suitable approach, including, for example, by a sensor (e.g., transmitting device 102) sensing a user's movement and transmitting information related to the user's movement to electronic device 250 for processing and storage in storage component 161. The user may start the workout immediately after storing the workout template in the electronic device or, alternatively, the user may start the workout at any time in the future by accessing the stored workout template. Process 2400 may advance to step 2416 and end.

Figure 19:
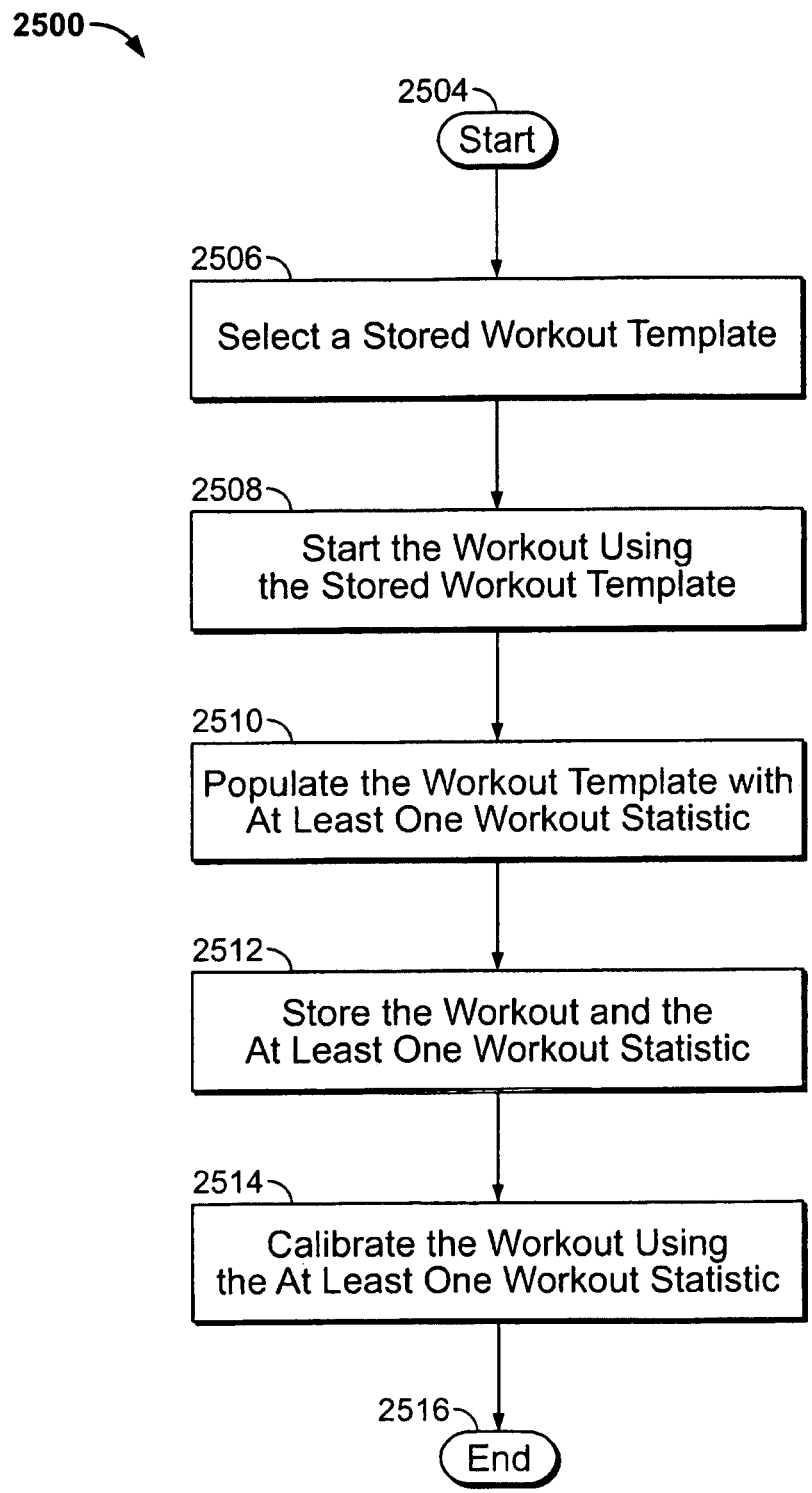
FIG. 19 is a flowchart of an illustrative process for performing a calibration in accordance with some embodiments of the invention.

FIG. 19 is a flowchart of an illustrative process for performing a calibration in accordance with some embodiments of the invention. Process 2500 may begin at step 2504. At step 2506, a workout template that may have been stored in the electronic device may be selected. For example, a user of electronic device 250 may select a workout template that was just created (e.g., using display screens 200 through 900) and stored in storage component 161 to quick start a workout on electronic device 250. Alternatively, the user may select a workout template that was stored in storage component 161 in the past and may have already been accessed at least once in quick starting a workout on electronic device 250.

Process 2500 may advance to step 2508, where the workout may start using the workout template that may be stored in the electronic device. The workout may be started using any suitable approach, including, for example, by electronic device 250 starting a clock or starting to track a distance or a user's activity, which may involve a sensor (e.g., transmitting device 102, FIG. 1A) sensing a user's movement and transmitting information related to the user's movement to electronic device 250.

In some embodiments (not shown), the workout may be displayed using any suitable approach. For example, electronic device 250 may include a display screen (e.g., display screen 1000, FIG. 10) that may display any suitable information to the user during the workout. For example, the display screen may present the user's traveled distance, the pace, the elapsed time, the media that may be associated with the workout because of the workout template that may have been selected at step 2504, and any other suitable information.

Process 2500 may advance to step 2510, where the selected workout template may be populated with at least one workout statistic generated from the workout in any suitable manner. For example, the workout may be performed in conjunction with any suitable sensor (e.g., transmitting device 102). As the workout progresses, electronic device 250 may receive information related to the workout from transmitting device 102. The information may be detected by transmitting device 102 in any suitable manner, including for example, in response to sensing the user's movement. Transmitting device 102 may transmit the information related to the workout to electronic device 250 in any suitable format and electronic device 250 may perform any suitable operations on the information to generate at least one workout statistic (e.g., a statistic related to the user's pace, the distance traveled, the time elapsed, or a particular activity on an exercise machine) that may then be stored in storage component 161.

Process 2500 may advance to step 2512, where the information (e.g., the at least one workout statistic) from step 2510 and the performed workout may be stored in the electronic device, including for example, in storage component 161. In some embodiments, the workout and the statistics generated during the workout may be stored in the electronic device regardless of whether the workout was completed. The workout and the related statistics may be reviewed in the future by the user and may be uploaded to any suitable remote network for sharing with other users. The workout template used in conjunction with the workout also may be accessed again by the user in the future to quick start a new workout using the workout template.

Process 2500 may advance to step 2514, where the electronic device may be calibrated using the information in any suitable manner. For example, if the at least one workout statistic reported by electronic device 250 does not match the actual value of the statistic (e.g., the electronic device reports that the user ran 9.8 miles and the user actually ran 10.0 miles), the user may calibrate electronic device 250 using the actual value of the at least one workout statistic. For example, the user may calibrate electronic device 250 as described above with respect to display screens 1200 through 1400. Process 2500 may then advance to step 2516 and end. In some embodiments (not shown), the user may review the stored workout statistic and may determine that the electronic device does not need to be calibrated, in which case, process 2500 may advance to step 2516 and end.

Figure 20:
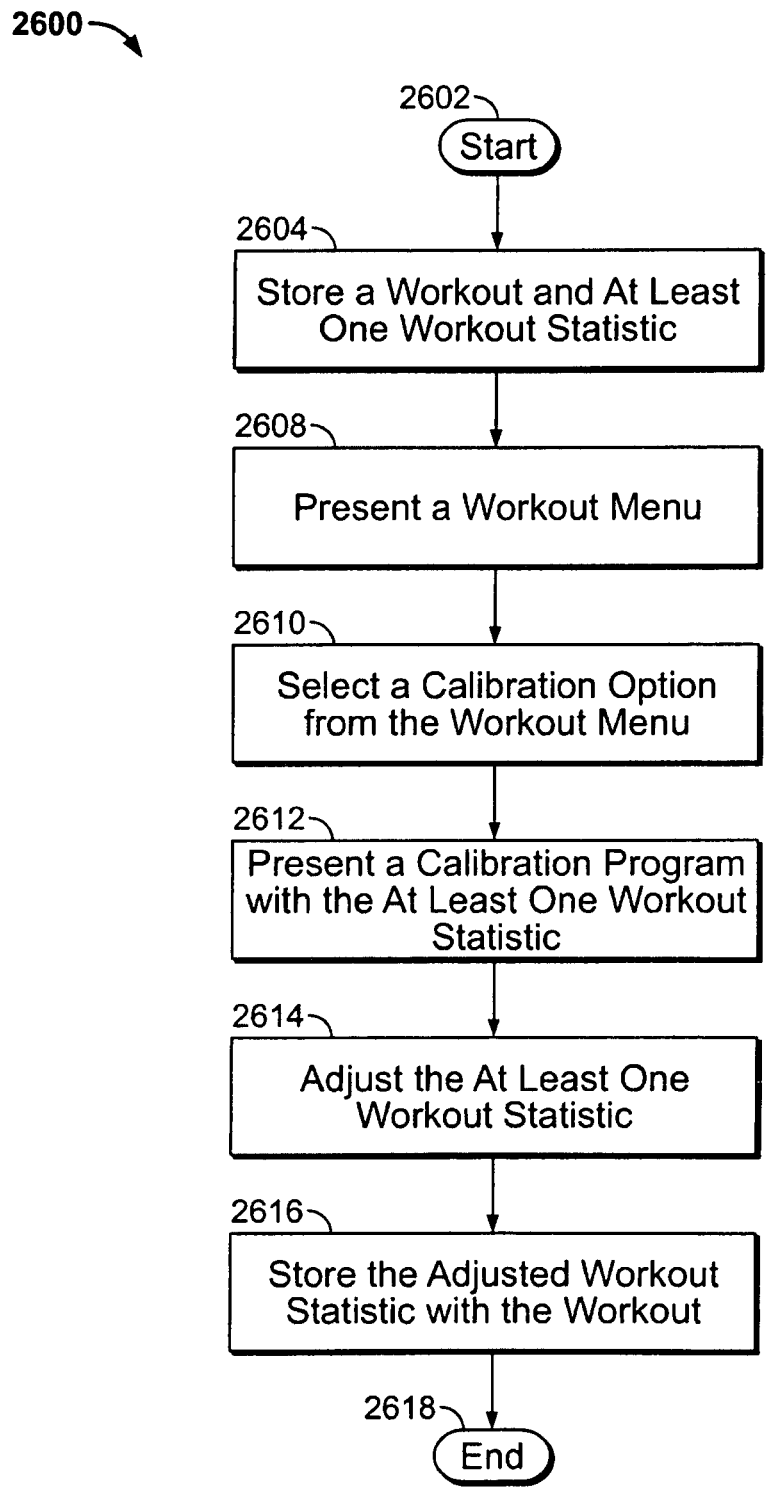
FIG. 20 is a flowchart of an illustrative process for calibrating an electronic device in accordance with some embodiments of the invention.

FIG. 20 is a flowchart of an illustrative process for calibrating an electronic device in accordance with some embodiments of the invention. Process 2600 may begin at step 2602. At step 2604, a performed workout and at least one workout statistic related to the workout may be stored in an electronic device. For example, a user of electronic device 250 may start a workout using a workout template and may either complete the entire workout or may otherwise end or pause the workout in any suitable fashion. While the workout is ongoing, any suitable sensor (e.g., transmitting device 102) may transmit information related to the user's movement during the workout to electronic device 250. Electronic device 250 may process that information into at least one workout statistic that may be stored in storage component 161 along with the completed or otherwise ended or paused workout.

Process 2600 may advance to step 2608, where a workout menu may be presented to the user after the workout and the at least one workout statistic have been stored in the electronic device. For example, the workout menu (e.g., display screen 1350) may be automatically presented to the user of electronic device 250 after the workout is ended or paused. Alternatively, the user may provide any suitable input (e.g., a press of click or scroll wheel 252 or button 254, a verbal command, or a touch to a display screen) to request that the workout menu be presented. The workout menu may include any suitable options that may depend on the context in which the workout menu is presented. For example, since the menu is presented during the workout or following the workout, the menu may include options such as "Save Workout," "Delete Workout," "Calibrate Workout," "Cancel," or any other suitable option reflecting the possible choices available to the user during or after the workout.

Process 2600 may advance to step 2610, where a calibration option may be selected from the workout menu. For example, the user of electronic device 250 may select "Calibrate Workout" from workout menu 1350. In response to the user selecting a calibration option from the workout menu, process 2600 may advance to step 2612, where a calibration program may be presented with the at least one workout statistic. For example, electronic device 250 may display the at least one workout statistic previously stored in storage component 161. Electronic device 250 also may provide any suitable means for adjusting the stored at least one workout statistic (e.g., arrows that may be operated by click or scroll wheel 252 or button 254) so that it reflects the actual value of the workout statistic.

Process 2600 may advance to step 2614, where the stored at least one workout statistic may be adjusted in any suitable manner. For example, the at least one workout statistic may represent a distance traveled by the user during the workout. The value of the stored workout statistic may be adjusted (e.g., increased or decreased) to reflect the correct value of the workout statistic (e.g., the actual distance that the user traveled during the workout). In some embodiments, any suitable number of workout statistics may be saved with respect to a workout and step 2614 may be repeated (not shown) to permit each of the workout statistics to be adjusted in a similar manner. For example, in addition to storing a distance traveled, electronic device 250 may also store a time elapsed with respect to the workout, and may permit the user to adjust the reported time to reflect the correct time elapsed during the workout.

Process 2600 may advance to step 2616, where the adjusted at least one workout statistic may be stored with the workout in any suitable manner. For example, the adjusted value of the at least one workout statistic may be stored in storage component 161 with the workout. Thereafter, the adjusted at least one workout statistic may be used in any suitable manner (e.g., to calibrate how electronic device 250 measures distance based on workout-related information received from the sensor). Process 2600 may then advance to step 2618 and end.

While there have been described systems and methods for creating and calibrating quick start workout templates, it is to be understood that many changes may be made therein without departing from the spirit and scope of the invention. It will also be understood that various directional and orientational terms such as "up" and "down," "left" and "right," "top" and "bottom," "side" and "edge" and "corner," "height" and "width" and "depth," "horizontal" and "vertical," and the like are used herein only for convenience, and that no fixed or absolute directional or orientational limitations are intended by the use of these words. For example, the positioning of a display screen within an electronic device and various icons contained within a display screen may have any desired orientation. If reoriented, different directional or orientational terms may need to be used in their description, but that will not alter their fundamental nature as within the scope of the invention. Those skilled in the art will appreciate that the invention can be practiced by other than the described embodiments, which are presented for purposes of illustration rather than of limitation, and the invention is limited only by the claims which follow.

What is claimed is:

1. A method for calibrating an electronic device, the method comprising:
    storing a workout and at least one workout statistic to the electronic device;
    retrieving the stored workout and the at least one workout statistic;
    presenting a workout menu in response to the retrieving of the workout and the at least one workout statistic;
    presenting a calibration program with the at least one workout statistic in response to a user selection of a calibration option from the workout menu;
    adjusting a measure of the at least one workout statistic based at least in part on an adjustment input using the calibration program; and
    storing the adjusted measure of the at least one workout statistic with the workout to the electronic device to calibrate the electronic device for the stored workout.

2. The method of claim 1, further comprising receiving with the electronic device the at least one workout statistic from a transmitting device.

3. The method of claim 2, wherein the at least one workout statistic is generated by the transmitting device in response to a user movement.

4. The method of claim 1, wherein the presenting the workout menu comprises:
    presenting a save option;
    presenting a delete option;
    presenting a cancel option; and
    presenting the calibration option.

5. The method of claim 1, wherein the at least one workout statistic comprises a distance traveled, a time elapsed, a pace, a number of calories burned, a measure of an activity performed on an exercise machine, or a combination thereof.

6. The method of claim 1, wherein the adjusting the at least one workout statistic comprises altering a reported value of the at least one workout statistic to correspond with an actual value from the workout.

7. An electronic device for calibrating a workout, the electronic device comprising:
    a storage component; and
    control circuitry coupled to the storage component, wherein the control circuitry is configured to:
        present a plurality of user-selectable workouts stored in the storage component;
        generate at least one workout statistic for one of the plurality of user-selectable workouts in response to a user selection of the one of the plurality of user-selectable workouts via the electronic device;
        present a calibration program with the at least one workout statistic and the selected one of the plurality of user-selectable workouts to calibrate the at least one workout statistic;
        adjust a recorded measure of the at least one workout statistic to correspond to an adjustment input value of the at least one workout statistic; and
        store the adjusted recorded measure of the at least one workout statistic with the selected one of the plurality of user-selectable workouts in the storage component.

8. The electronic device of claim 7, wherein the control circuitry is further operative to:
    receive information about the workout from a transmitting device; and
    generate the at least one workout statistic from the workout in response to receiving the information.

9. The electronic device of claim 8, wherein the control circuitry is operative to present the at least one workout option in the form of a menu.

10. The electronic device of claim 8, wherein the control circuitry is further operative to:
    compare the reported value to the actual value;
    determine that the reported value does not equal the actual value; and
    increase or decrease the reported value to correspond to the actual value.

11. A method, comprising:
    receiving a user selection of a workout of a plurality of workouts stored to an electronic device;
    generating a plurality of workout statistics based at least in part on the selected workout and corresponding to user performance of the selected workout;
    presenting a workout summary screen comprising the plurality of workout statistics and the selected workout;
    presenting a calibration screen to calibrate at least one workout statistic of the plurality of workout statistics, wherein the calibration screen comprises the selected workout and a recorded measure of the at least one workout statistic, and wherein the at least one workout statistic comprises a number of calories burned, a measure of an activity performed on an exercise machine, or a combination thereof;
    adjusting the recorded measure of the at least one workout statistic to correspond to an adjustment input value of the at least one workout statistic; and
    storing the adjusted recorded measure of the at least one workout statistic with the selected workout.

* * * * *